United States Patent [19]
Ito et al.

[11] Patent Number: 5,104,531
[45] Date of Patent: Apr. 14, 1992

[54] CROSS-AXIS SYNCHRONOUS FLOW THROUGH COIL PLANET CENTRIFUGE FOR LARGE SCALE PREPARATIVE COUNTERCURRENT CHROMATOGRAPHY

[75] Inventors: Yoichiro Ito, Bethesda, Md.; Tian Y. Zhang, Beijing, China

[73] Assignee: The United States of America as represented by the Department of Health and Human Services, Washington, D.C.

[21] Appl. No.: 742,500

[22] Filed: Aug. 5, 1991

Related U.S. Application Data

[63] Continuation of Ser. No. 488,464, Feb. 26, 1990, abandoned, which is a continuation of Ser. No. 304,853, Jan. 30, 1989, abandoned.

[51] Int. Cl.$^5$ ............................................. B01D 15/08
[52] U.S. Cl. ................................. 210/198.2; 210/657
[58] Field of Search ..................... 210/657, 198.2, 635; 55/386

[56] References Cited

U.S. PATENT DOCUMENTS

| | | | |
|---|---|---|---|
| 3,775,309 | 11/1973 | Ito | 210/657 |
| 3,856,669 | 12/1974 | Ito | 210/657 |
| 3,994,805 | 11/1976 | Ito | 210/657 |
| 4,051,025 | 9/1977 | Ito | 210/657 |
| 4,058,460 | 11/1977 | Ito | 210/198.2 |
| 4,321,138 | 3/1982 | Ito | 210/657 |
| 4,487,693 | 12/1984 | Ito | 210/657 |
| 4,615,805 | 10/1986 | Ito | 210/657 |
| 4,714,554 | 12/1987 | Ito | 210/198.2 |
| 4,753,734 | 6/1988 | Ito | 210/657 |

*Primary Examiner*—Ernest G. Therkorn
*Attorney, Agent, or Firm*—Lowe, Price, LeBlanc & Becker

[57] ABSTRACT

A countercurrent chromatography apparatus and method where the column rotates about an axis spaced apart from, parallel to, and in the same radial plane as a radius extending from the central axis of revolution. The apparatus generates a unique force field which enables excellent separation.

6 Claims, 25 Drawing Sheets

$\beta = r/R$

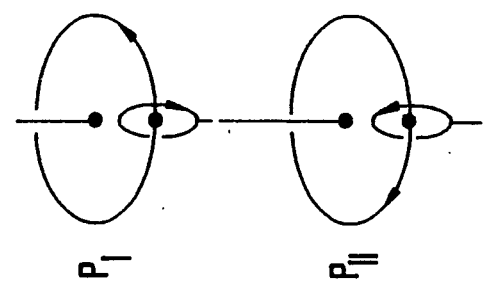

FIG.9

| PLANETARY MOTION | HEAD-TAIL ELUTION MODE | INWARD-OUTWARD ELUTION MODE (HANDEDNESS OF COIL*) | COMBINED ELUTION MODE** | SYMBOLIC SIGNS IN PDD*** |
|---|---|---|---|---|
| $P_I$ | HEAD → TAIL<br>HEAD → TAIL<br>TAIL → HEAD<br>TAIL → HEAD | INWARD (R)<br>OUTWARD (L)<br>INWARD (L)<br>OUTWARD (R) | $P_I$–H–I<br>$P_I$–H–O<br>$P_I$–T–I<br>$P_I$–T–O | 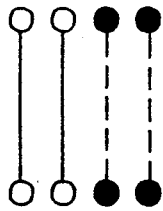 |
| $P_{II}$ | HEAD → TAIL<br>HEAD → TAIL<br>TAIL → HEAD<br>TAIL → HEAD | INWARD (L)<br>OUTWARD (R)<br>INWARD (R)<br>OUTWARD (L) | $P_{II}$–H–I<br>$P_{II}$–H–O<br>$P_{II}$–T–I<br>$P_{II}$–T–O |  |

\* R: RIGHT-HANDED; L: LEFT-HANDED
\*\* H: HEAD — T: TAIL — I: INWARD; O: OUTWARD
\*\*\* PDD: PHASE DISTRIBUTION DIAGRAM

| HEXANE / WATER | HEXANE / METHANOL | EtOAc / H₂O | EtOAc:AcOH:H₂O 4:1:4 | CHCl₃ / H₂O |
|---|---|---|---|---|
| $P_I$ -T-0:97.2 | $P_I$ -T-0:85.0 | $P_I$ -T-0:91.0 | $P_I$ -T-1:87.0 | $P_I$ -T-1:96.0 |
| $P_I$ -T-1:96.9 | $P_I$ -T-0:83.1 | $P_I$ -T-1:89.8 | $P_I$ -T-0:86.4 | $P_I$ -T-0:95.5 |
| $P_{II}$ -T-0:94.4 | $P_{II}$ -T-1:74.3 | $P_{II}$ -T-1:85.9 | $P_{II}$ -T-1:74.6 | $P_{II}$ -T-0:94.4 |
| $P_{II}$ -T-1:94.4 | $P_{II}$ -T-0:49.2 | $P_{II}$ -T-0:85.3 | $P_{II}$ -T-0:61.6 | $P_{II}$ -T-1:87.6 |
| $P_I$ -H-0:1.7 | $P_{II}$ -H-1:27.1 | $P_I$ -H-0:2.3 | $P_{II}$ -H-1:20.9 | $P_{II}$ -H-0:10.2 |
| $P_{II}$ -H-1:1.7 | $P_{II}$ -H-0:20.9 | $P_I$ -H-1:1.7 | $P_{II}$ -H-0:18.4 | $P_{II}$ -H-1:9.6 |
| $P_I$ -H-0:1.7 | $P_I$ -H-0:6.2 | $P_{II}$ -H-1:1.7 | $P_I$ -H-0:7.9 | $P_I$ -H-0:3.9 |
| $P_{II}$ -H-1:0.6 | $P_I$ -H-1:0.8 | $P_{II}$ -H-0:0.6 | $P_I$ -H-1:5.1 | $P_I$ -H-1:3.4 |

UPPER PHASE MOBILE

FIG.12A

| | CHCl₃ AcOH H₂O  2 2 1 | n-BuOH  H₂O | n-BuOH AcOH H₂O  4 1 5 | sec.-BuOH  H₂O |
|---|---|---|---|---|
| | P$_{II}$ -H-I:65.0 | P$_I$ -T-I:77.4 | P$_{II}$ -H-I:64.1 | P$_I$ -H-0:52.5 |
| | P$_{II}$ -H-0:64.4 | P$_I$ -T-0:71.5 | P$_{II}$ -H-0:62.1 | P$_I$ -H-I:49.2 |
| | P$_I$ -T-I:57.3 | P$_{II}$ -H-0:30.2 | P$_{II}$ -H-0:46.9 | P$_{II}$ -H-0:47.5 |
| | P$_I$ -T-0:46.6 | P$_{II}$ -H-I:17.8 | P$_I$ -H-I:33.7 | P$_{II}$ -H-I:45.8 |
| | P$_I$ -H-0:24.3 | P$_{II}$ -T-0:10.2 | P$_I$ -T-I: 7.6 | P$_I$ -T-0: 8.2 |
| | P$_{II}$ -H-I:21.5 | P$_I$ -H-0: 9.0 | P$_I$ -T-I: 7.3 | P$_{II}$ -T-0: 6.2 |
| | P$_{II}$ -T-I: 0 | P$_I$ -H-0: 8.0 | P$_I$ -T-0: 4.5 | P$_{II}$ -T-0: 0.8 |
| | P$_{II}$ -T-0: 0 | P$_I$ -H-I: 7.3 | P$_{II}$ -T-0: 1.1 | P$_I$ -T-I: 0.6 |

UPPER PHASE MOBILE

FIG.12B

| HEXANE / WATER | | HEXANE / METHANOL | | EtOAc / H₂O | | EtOAc / AcOH / H₂O (4:1:4) | | CHCl₃ / H₂O | |
|---|---|---|---|---|---|---|---|---|---|
| $P_I$ -H-0:94.4 | $P_I$ -H-0:89.8 | $P_I$ -H-I:93.5 | $P_I$ -H-I:78.5 | $P_I$ -H-0:94.9 |
| $P_I$ -H-I:93.5 | $P_I$ -H-0:89.3 | $P_I$ -H-0:92.1 | $P_I$ -H-0:70.6 | $P_I$ -H-I:93.8 |
| $P_{II}$ -H-I:90.1 | $P_{II}$ -H-0:56.5 | $P_I$ -H-0:87.3 | $P_{II}$ -H-0:45.2 | $P_I$ -H-0:87.0 |
| $P_{II}$ -H-0:89.8 | $P_{II}$ -H-I:51.4 | $P_{II}$ -H-I:85.3 | $P_{II}$ -H-I:27.1 | $P_{II}$ -H-I:87.0 |
| $P_{II}$ -T-0: 2.8 | $P_{II}$ -T-0:17.5 | $P_{II}$ -T-I: 9.3 | $P_{II}$ -T-0:14.7 | $P_{II}$ -T-I:22.6 |
| $P_I$ -T-I: 2.3 | $P_I$ -T-I:16.9 | $P_{II}$ -T-0: 8.5 | $P_{II}$ -T-I:11.0 | $P_{II}$ -T-0:17.7 |
| $P_{II}$ -T-I: 2.0 | $P_I$ -T-0:13.3 | $P_I$ -T-0: 6.8 | $P_I$ -T-0: 7.9 | $P_I$ -T-0:10.2 |
| $P_I$ -T-0: 2.0 | $P_I$ -T-0: 9.0 | $P_I$ -T-I: 5.6 | $P_I$ -T-I: 5.6 | $P_I$ -T-0: 6.8 |

LOWER PHASE MOBILE

FIG.12C

| CHCl₃ 2<br>AcOH 2<br>H₂O 1 | n-BuOH<br><br>H₂O | n-BuOH 4<br>AcOH 1<br>H₂O 5 | sec.-BuOH<br><br>H₂O |
|---|---|---|---|
| $P_I$ -H-I:74.9 | $P_I$ -H-I:88.7 | $P_{II}$ -T-0:78.5 | $P_{II}$ -T-I:61.6 |
| $P_I$ -H-0:58.2 | $P_I$ -H-0:84.7 | $P_{II}$ -T-I:75.7 | $P_I$ -T-0:58.2 |
| $P_{II}$ -T-I:35.0 | $P_{II}$ -H-I:40.7 | $P_{II}$ -T-I:58.2 | $P_{II}$ -T-0:56.5 |
| $P_{II}$ -T-0:33.1 | $P_{II}$ -H-0:33.3 | $P_I$ -T-0:57.1 | $P_I$ -T-I:55.9 |
| $P_I$ -T-0:32.2 | $P_{II}$ -T-0:25.4 | $P_{II}$ -H-I:10.7 | $P_{II}$ -H-I: 8.5 |
| $P_I$ -T-I:24.3 | $P_I$ -T-0:16.9 | $P_{II}$ -H-0: 7.3 | $P_I$ -H-I: 6.8 |
| $P_{II}$ -H-I:14.7 | $P_I$ -T-0:16.1 | $P_I$ -H-I: 2.0 | $P_{II}$ -H-0: 5.1 |
| $P_{II}$ -H-0:10.1 | $P_I$ -T-I:15.3 | $P_I$ -H-0: 1.7 | $P_I$ -H-0: 3.9 |

LOWER PHASE MOBILE

FIG.12D

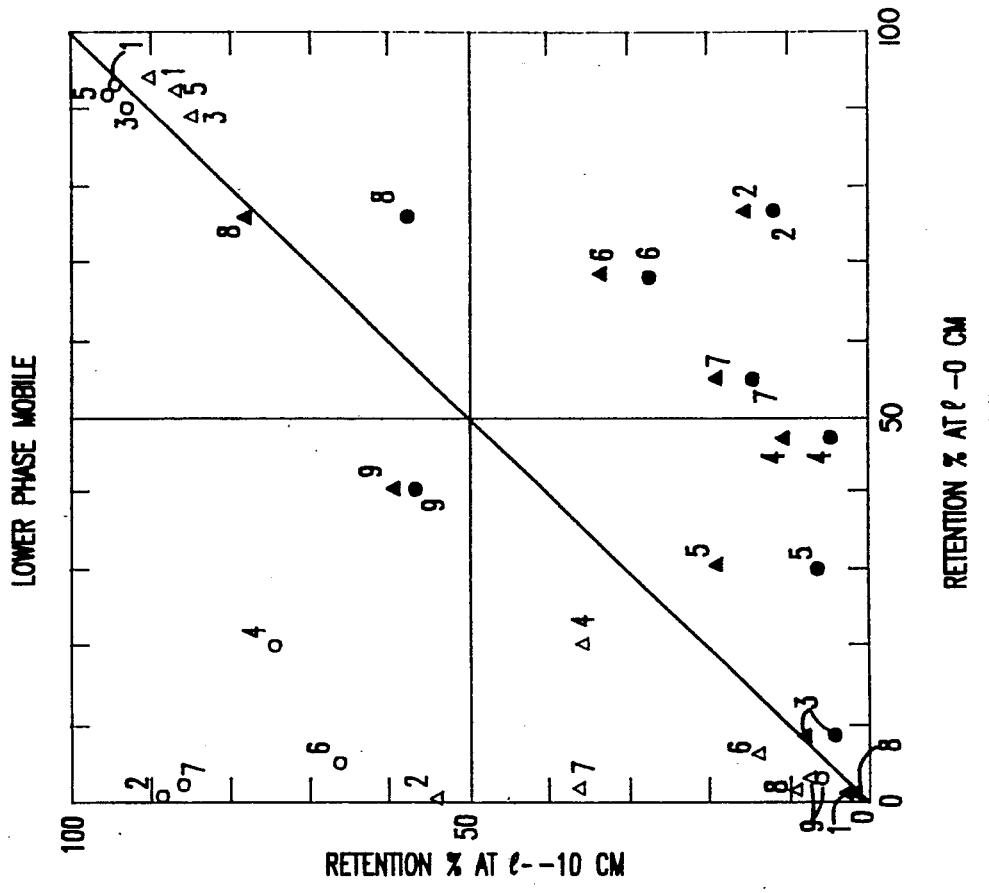
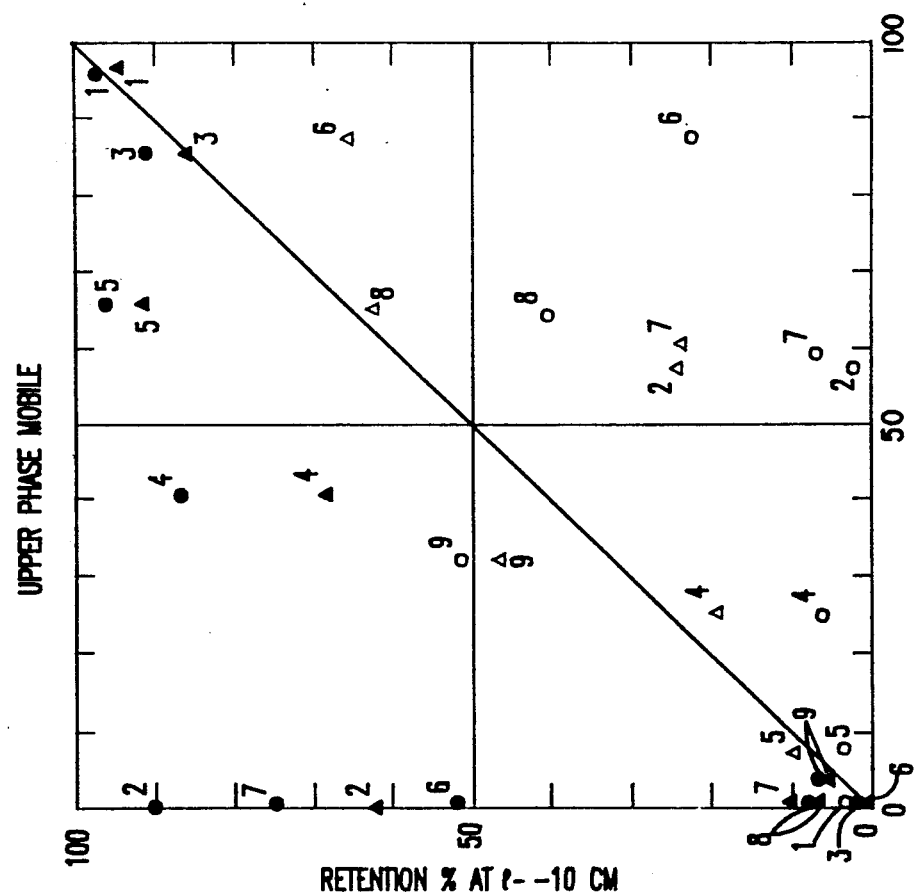
FIG.15A
FIG.15B

CROSS-AXIS SYNCHRONOUS FLOW THROUGH COIL PLANET CENTRIFUGE FOR LARGE SCALE PREPARATIVE COUNTERCURRENT CHROMATOGRAPHY

This application is a continuation application of application Ser. No. 07/488,464, filed Feb. 26, 1990 which is a continuation application of Ser. No. 07/304,853 filed Jan. 30, 1989, both now abandoned.

BACKGROUND OF THE INVENTION

1. Field of the Invention

The present invention relates to methods and apparatus for centrifugal separation, and more particularly to toroidal coil centrifugation for the separation of particles and solutes from liquids.

2. Discussion of the Prior Art

Centrifugal countercurrent chromatography has been used in high efficiency analytical separation with a variety of single and two phase systems. In separation, it has been found that the geometry of the coiled column and the acting centrifugal force field play a major role in separation.

In some of the previous teachings relating to the use of toroidal coil centrifuges (for example, see Y. Ito, U.S. Pat. No. 4,051,025, Sept. 27, 1977; Ito et al., Science 189, 999 (1975); Ito et al., Anal. Biochem. 85, 614 (1978)), the coiled column is placed in the periphery of the rotating disc structure to produce a stable centrifugal force field where particles or stationary phase of a two-phase solvent system are retained in each coil unit favored by the acting direction of the force while the mobile phase is continuously eluted through the column. One of the disadvantages of this system is the lack of mixing force of the column contents which tends to produce inefficient separations.

Another type of system, called the horizontal flow-through coil planet centrifuge (e.g., see R. L. Bowman and Y. Ito, U.S. Pat. No. 3,775,309, Nov. 27, 1973; U.S. Pat. No. 3,994,805, Nov. 30, 1976, and Y. Ito, U.S. Pat. No. 4,058,460, Nov. 15, 1977), utilizes a coiled tube which synchronously rotates around its own axis in either the same direction or the opposite direction while revolving about the central axis of the centrifuge. Thus the planetary motion of the coiled column produces a rotating or oscillating centrifugal force field with respect to the coiled column.

U.S. Pat. No. 4,714,554, issued to the present inventor on Dec. 22, 1987 and incorporated herein by reference, discloses a method and apparatus for countercurrent chromatography which has proven useful in the efficient mixing of two solvent phases and which has been shown to improve retention of a stationary phase depending on the configuration of the coiled column on the rotating holder.

However, subsequent to the development of the invention disclosed in U.S. Pat. No. 4,714,554, a need has arisen to provide satisfactory retentions of stationary phases and particles in the fluctuating acceleration field produced by an apparatus of this kind, and especially for partitions in hydrophilic solvent systems which are extremely useful for separations of peptides and other polar compounds.

SUMMARY AND OBJECTS OF THE INVENTION

It is, therefore, an object of the present invention to overcome the above-noted deficiencies in the prior art, and to provide for improved separation of materials.

Another object of the present invention is to provide an improved system, and particularly an improved centrifugal apparatus, which utilizes a rotating coiled tube in a centrifugal force field for separation of particles and solutes.

Yet another object of the present invention is to provide improved control of the pattern of the centrifugal force field to obtain improved separation.

These and other objects are attained by the provision of a countercurrent centrifugal mechanism which is an improvement over the centrifugal mechanism disclosed in U.S. Pat. No. 4,714,554, issued on Dec. 22, 1987 to the inventor, and the disclosure of which is incorporated herein by reference. In particular, the objects of the present invention are achieved by the provision of a cross-axis synchronous flow-through coil planet centrifuge which includes, in a first embodiment, a pair of coil holders supported symmetrically about the central axis of the rotary frame, and in a second embodiment, one coil holder and a counterweight supported symmetrically about the central axis of the rotary frame. In each embodiment, structural means are provided to support the coil holder(s) on each side of the central axis. Preferably, and in accordance with the experiments carried out using this apparatus, the positioning of the coil holder(s) is laterally offset at about 12.5 cm from the center of the holder shaft and further offset at about 10 cm from the central axis of the rotary frame.

BRIEF DESCRIPTION OF THE DRAWINGS

Further objects and advantages of the invention will become apparent from the following description of the invention and from the accompanying drawings, in which:

FIG. 9 illustrates eight elution modes at the lateral coil position;

FIGS. 12A, 12B, 12C, and 12D are a table showing stationary phase retention in a lateral coil position;

FIGS. 15A and 15B illustrate stationary phase retention in short coils for $\beta = 0.625$, 25 cm holder;

DESCRIPTION OF THE DRAWINGS AND THE PREFERRED EMBODIMENT

Figure 1:
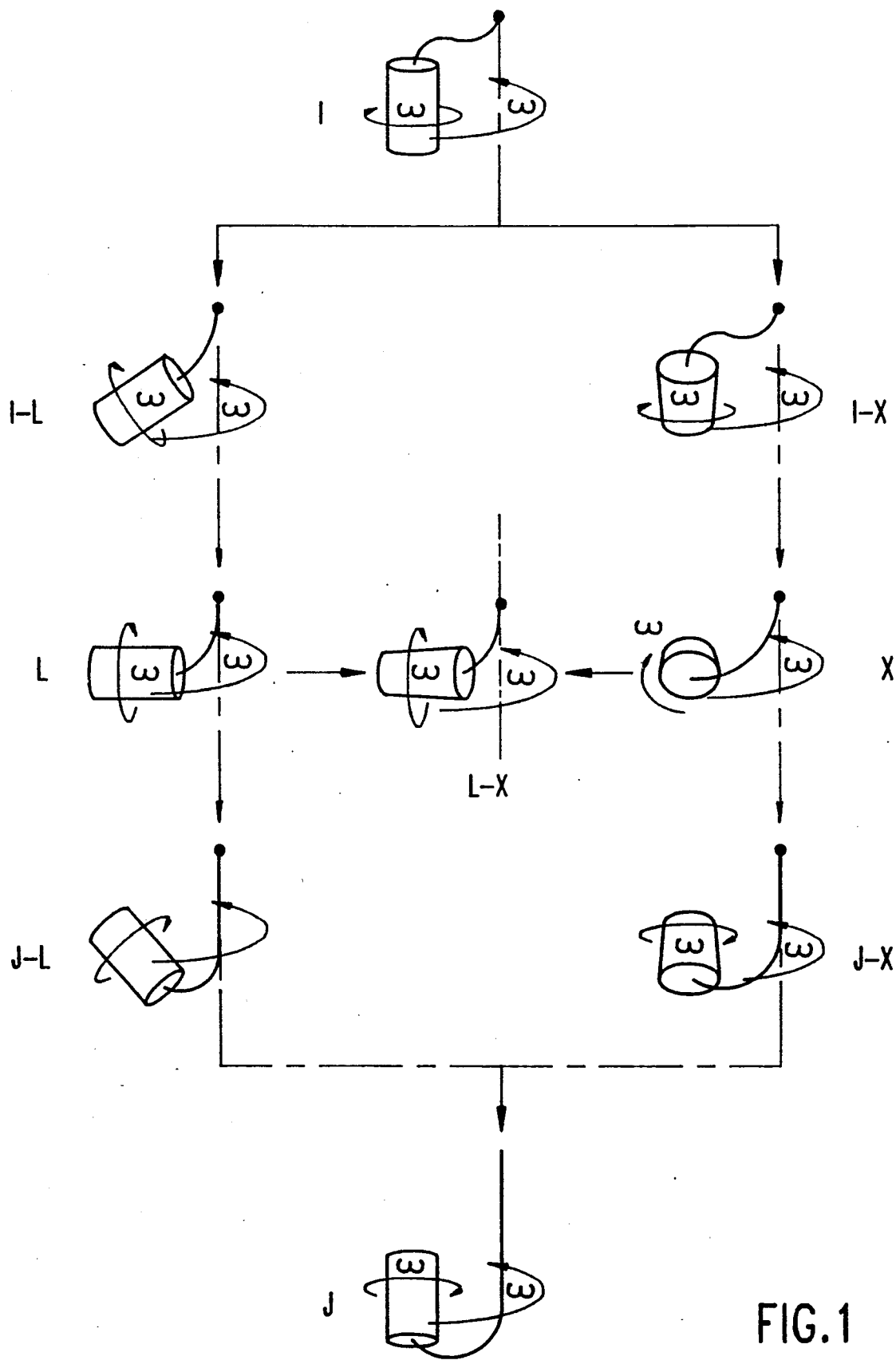
FIG. 1 schematically shows various planetary motion schemes.

Referring now to FIG. 1 of the drawings, there is shown a set of rotary seal free flow-through centrifuge systems developed for performing countercurrent chromatography (CCC). In each diagram, a cylindrical coil holder with a bundle of flow tubes revolves around the main axis of the centrifuge and simultaneously counter-rotates about its own axis at the same angular velocity. The bundle of flow tubes with one end tightly supported at the central axis above the centrifuge does not twist because the synchronous planetary motion of the holder steadily unwinds the twist of the tube bundle caused by the revolution. Consequently, all these systems permit continuous elution through the rotating column without the use of the rotary seal device which would become a potential source of various complications, such as leakage, contamination, etc.

The Type I systems shown at the top of FIG. 1 has a vertical orientation of the holder which can be modified in two different ways. In the left-hand column, the holders have been tilted toward the central axis of the centrifuge to form Types L and J and their hybrids, whereas in the right-handed column, the holders have been rotated sideways to form Types X and J and their hybrids. In the past, all of these centrifuge systems, with the exception of the systems labelled "I-X" and "J-X", were constructed for performing CCC. Of these CCC systems, those of type J and type X were found to be the most useful because of their unique capability to form unilateral distributions of the two solvent phases in the coiled column which is, in turn, utilized for performing high-speed CCC. The type J system is ideal for semi-preparative to analytical scale separations, while the type X system is most suitable for preparative scale separations.

Figure 2:
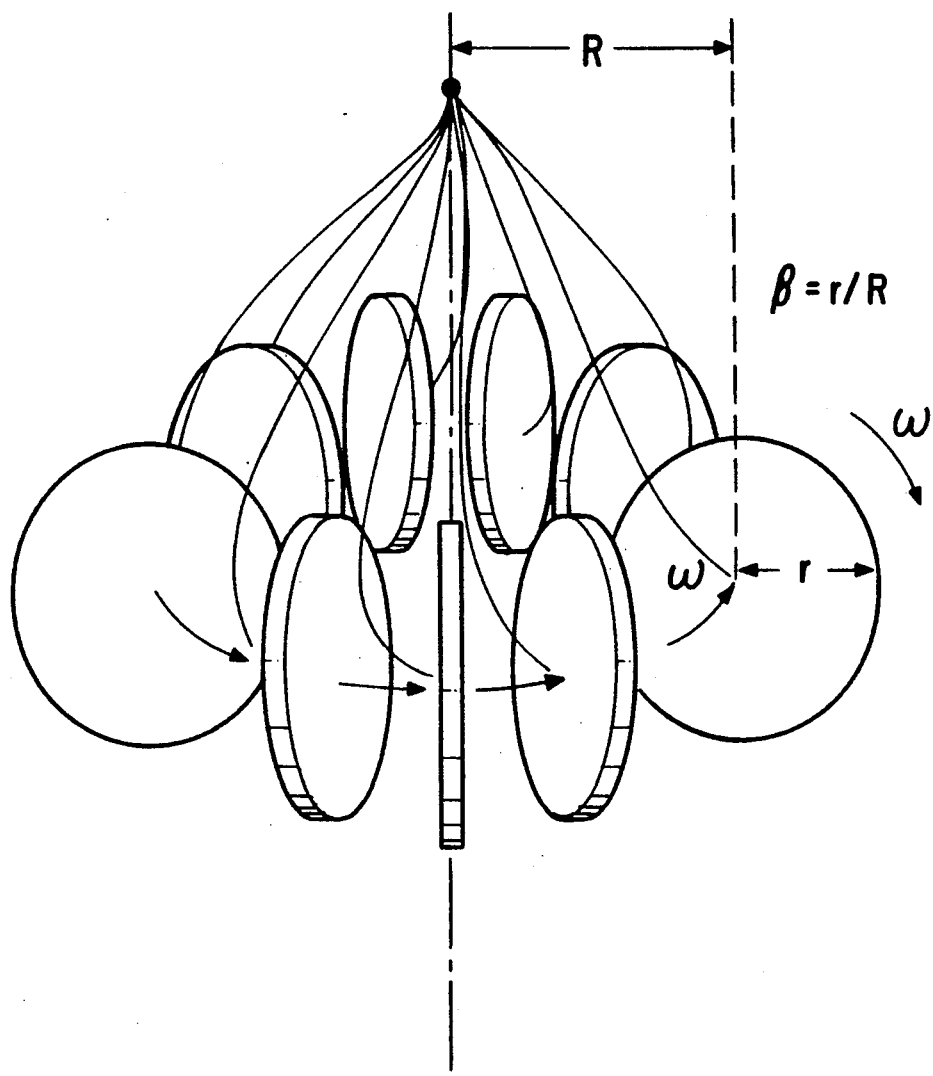
FIG. 2 schematically illustrates the successive positions of the coil holder disc of the present invention in its synchronous motion about the central axis of the centrifuge.

FIG. 2 illustrates the synchronous motion of the coil holder disc is schematically shown in various successive positions as it moves about the central axis of a centrifuge. The coil holder disc revolves about the central axis of the centrifuge at a predetermined angular velocity $\omega$ in a substantially counterclockwise direction, and simultaneously rotates in a substantially clockwise direction about its own axis at the same predetermined angular velocity 107. As a result of this compound motion, the axis of the coil holder disc is constantly maintained in a tangential orientation to the path of revolution of the coil holder disc about the centrifuge axis, at a preselected radius R from the centrifuge axis. Consequently, the axes of revolution and rotation in the planetary motion form a cross to each other, and hence the name of the apparatus.

The synchronous planetary motion exhibited by the apparatus illustrated in FIG. 2 has proven useful in providing two important functions in the process of countercurrent chromatography (CCC).

(1) first, the synchronous rotation of the holder disc steadily unwinds the twist of the tube bundle caused by the revolution, thus permitting continuous elution of the mobile phase through the rotating column. The elution takes place without the use of a conventional rotary seal device which could lead to such complications as, for example, leakage or contamination.

(2) Second, the planetary motion generates a unique pattern of the centrifugal force field which enables efficient chromatographic separations of solutes in a multilayer coil under a high flow rate of the mobile phase.

Figure 3A:
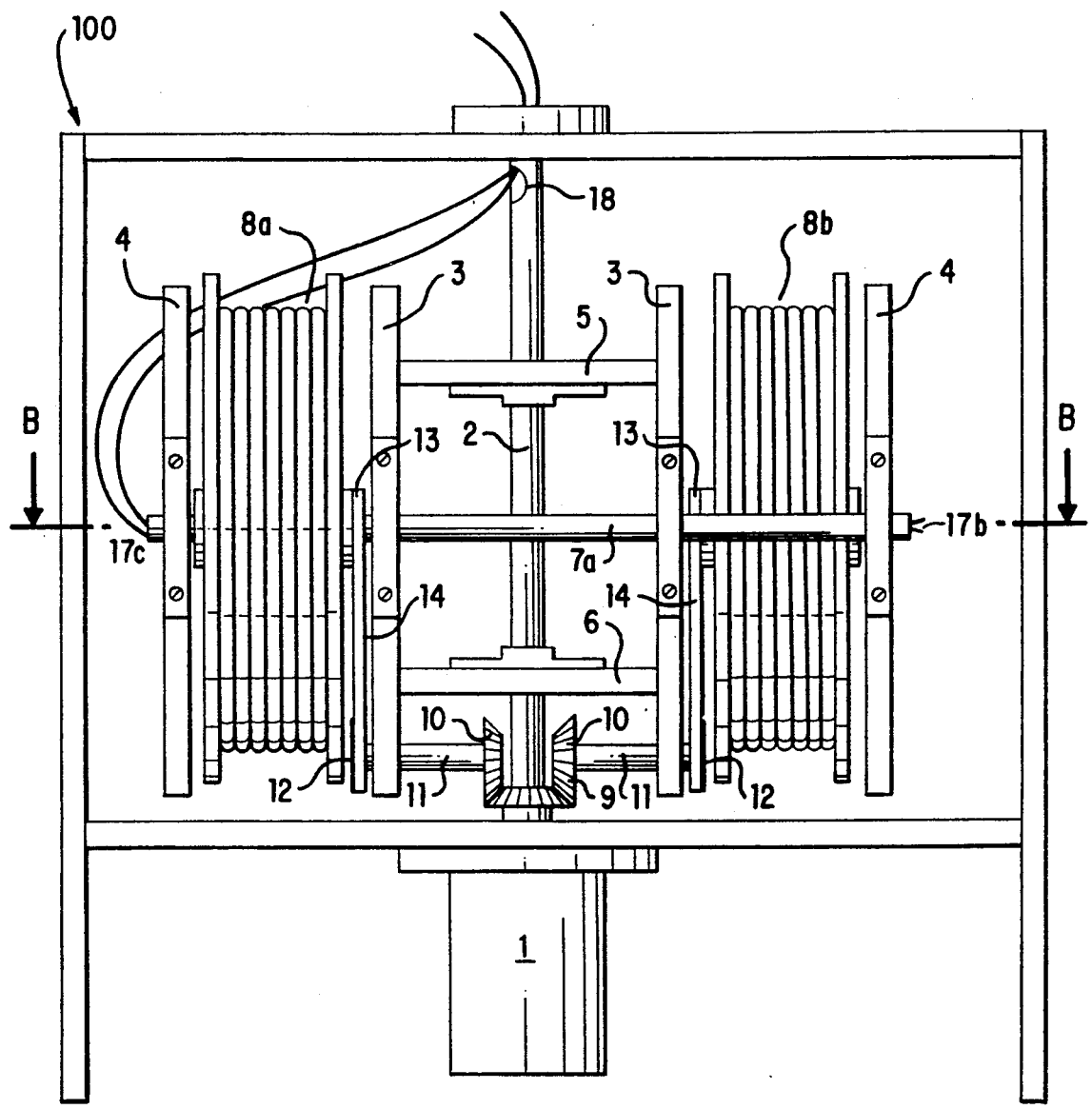
FIG. 3A is a side elevational view of a first embodiment of the present invention.
Figure 3B:
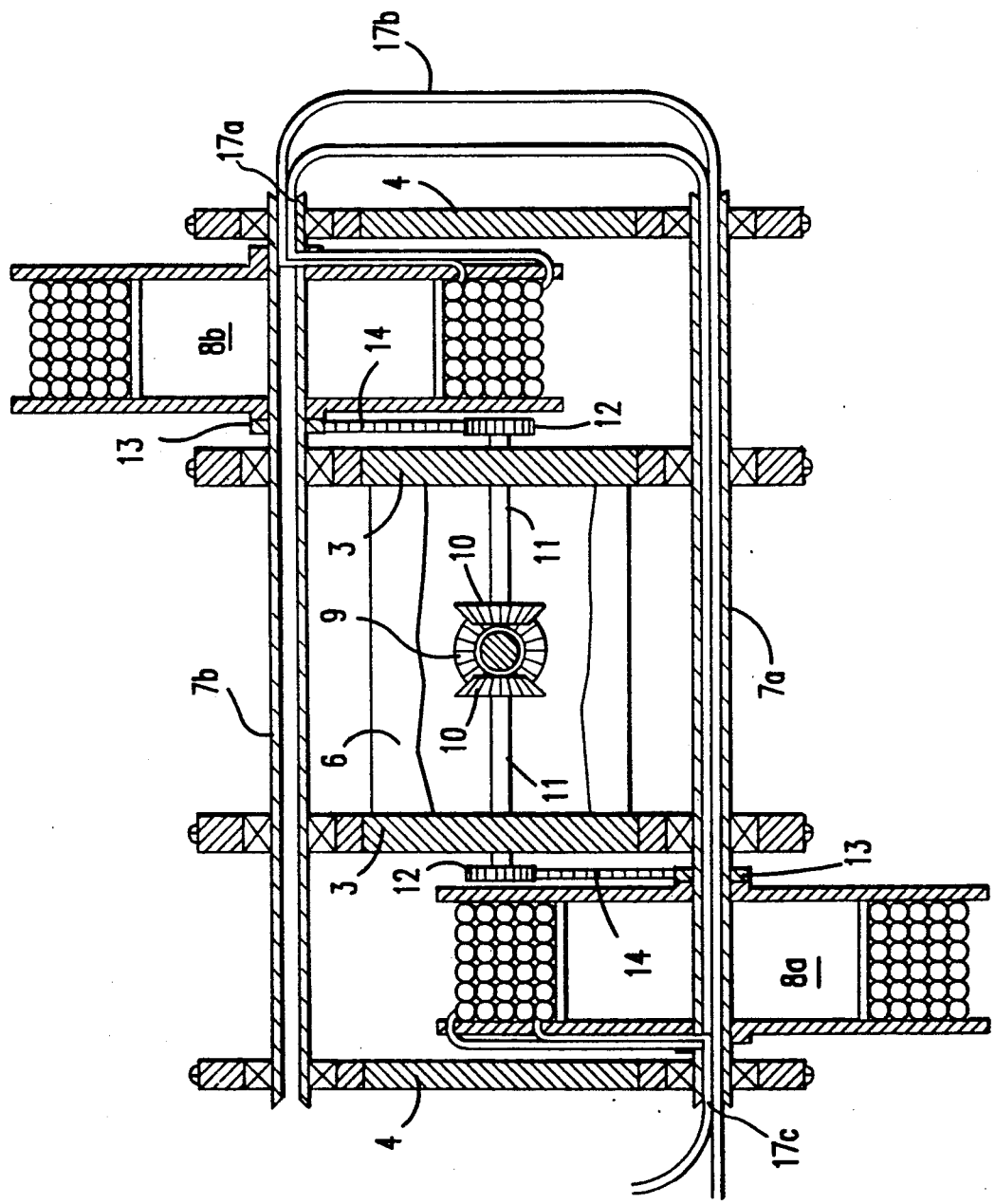
FIG. 3B is a cross-sectional view of the apparatus of FIG. 3A, taken along section line B—B.

Referring now to FIGS. 3A-3C, analysis of the acceleration field produced by the apparatus of the present system first requires examination of the hydrodynamics involved.

Figure 4A:
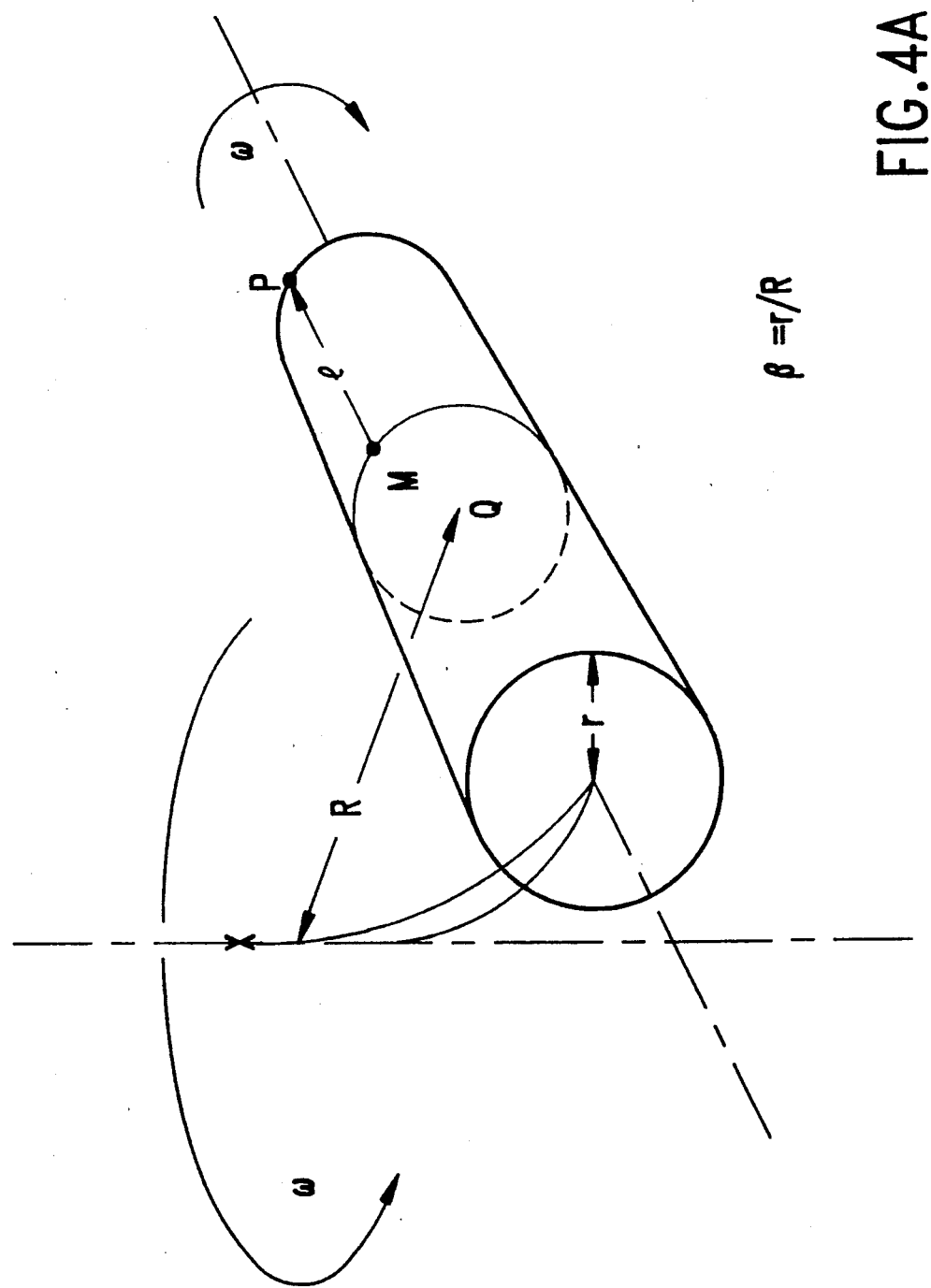
FIG. 4A is a schematic representation of the synchronous planetary motion experienced by a point P on a centrifuge.

As shown schematically in FIG. 4A, the cylindrical coil holder of a cross-axis coil planet centrifuge (CPC) exhibits planetary motion as it revolves around the central axis of the centrifuge system and simultaneously rotates about its own axis at the same angular velocity, $\omega$, in the indicated directions. While doing so, the cylinder maintains the axial orientation perpendicular to, and at a distance R from, the central axis of the centrifuge. The motion of an arbitrary point P, located at the periphery of the cylinder at a distance l from point M on the central plane, can be observed as the cylinder undergoes the planetary motion described above.

Figure 4B:
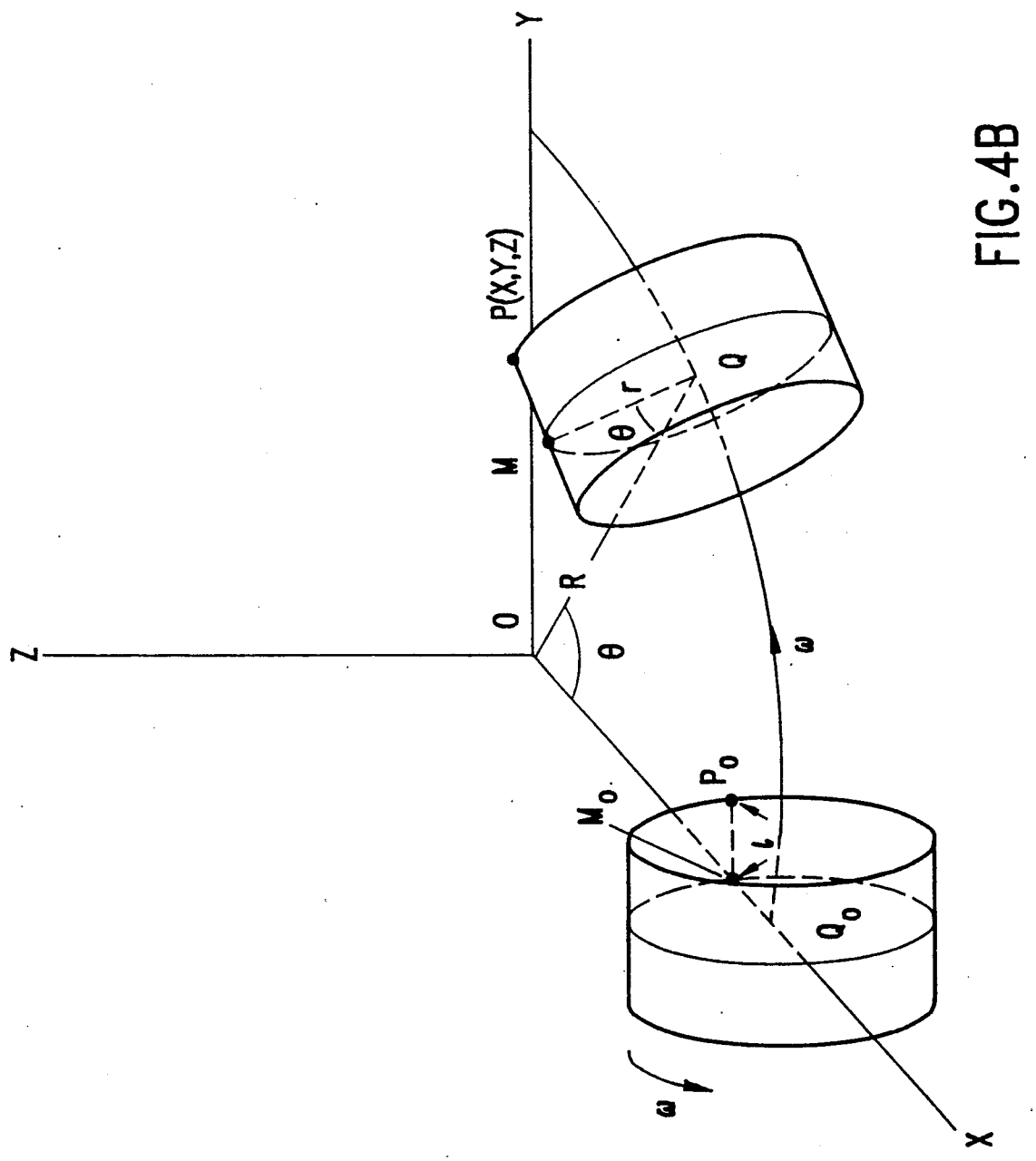
FIG. 4B schematically illustrates the synchronous planetary motion of the point P on a centrifuge according to the present invention, in the x-y-z coordinate system.

In the x-y-z coordinate system shown in FIG. 4B, the cylinder revolves around the z-axis at an angular velocity $\omega$ and simultaneously rotates about its own axis at the same angular velocity $\omega$. The arbitrary point on the coil holder initially assumes the position $P_o$ (R-r,l,O) and, after a lapse of time t, moves to point P (x,y,z) so that the following equations apply:

$$x = R \cos\theta - r \cos^2\theta - l \sin\theta \quad (1)$$

$$y = R \sin\theta - r \sin\theta \cos\theta + l \cos\theta \quad (2)$$

$$z = r \sin\theta \quad (3)$$

The acceleration acting on the arbitrary point is then obtained from the second derivatives of these equations, as follows:

$$d^2x/dt^2 = -R\omega^2(\cos\theta - 2\beta \cos 2\theta) + l\omega^2 \sin\theta \quad (4)$$

$$d^2y/dt^2 = -R\omega^2(\sin\theta - 2\beta \sin 2\theta) - l\omega^2 \cos\theta \quad (5)$$

$$d^2z/dt^2 = -R\omega^2\beta \sin\theta \quad (6)$$

where $\beta = r/R$.

Figure 4C:
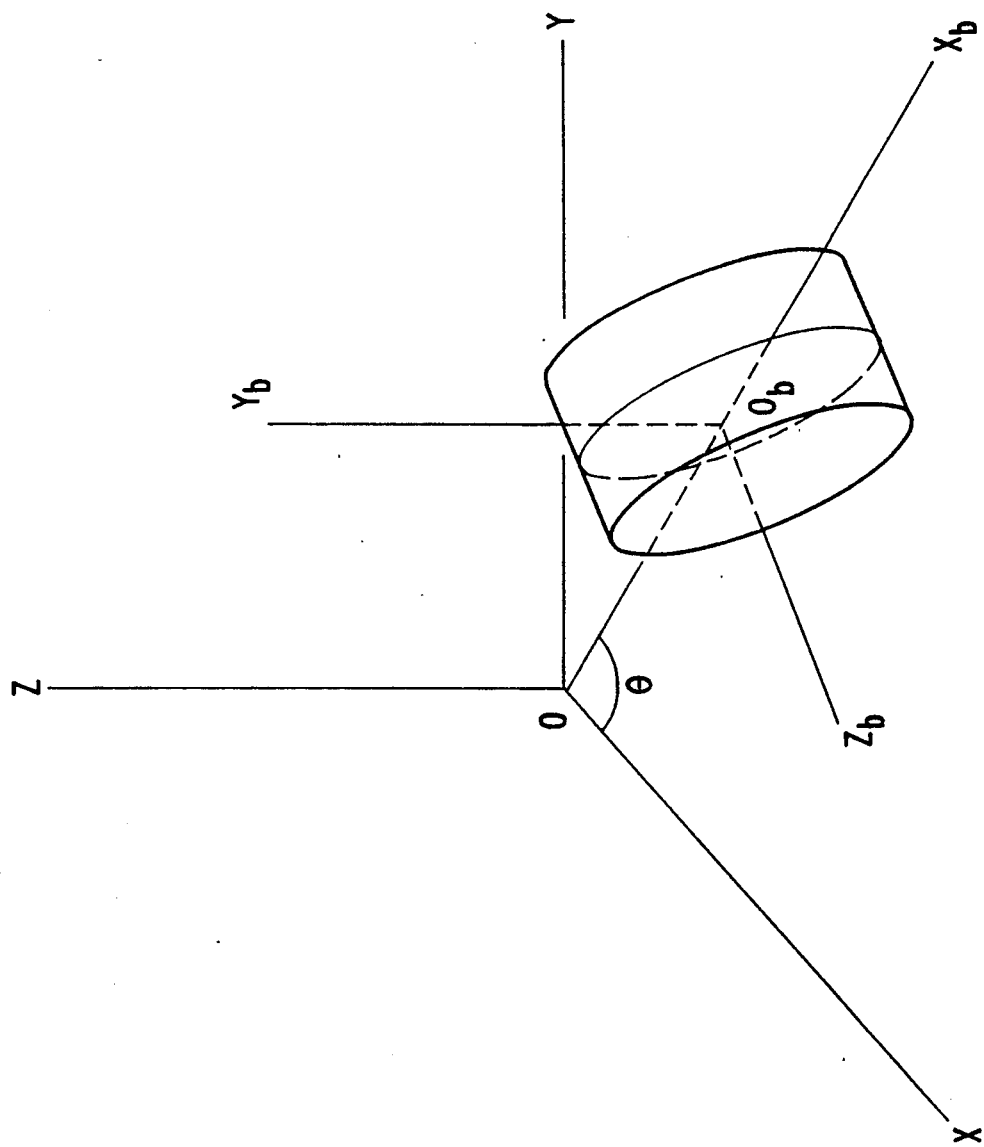
FIG. 4C schematically illustrates the motion illustrated in FIG. 4B, in the $x_b$-$y_b$-$z_b$ coordinate system.

In order to visualize the effects of acceleration on the objects rotating with the cylinder, it is more appropriate to express the acceleration vectors with respect to the body frame or the $x_b$-$y_b$-$z_b$ coordinate system illustrated in FIG. 4C. Transformation of the vectors from the original reference system to the body coordinate system may be performed according to the following equations:

$$a_{x\beta} = (d^2x/dt^2) \cos\theta + (d^2y/dt^2) \sin\theta = -R\omega^2(1 - 2\beta \cos\theta) \quad (7)$$

$$a_{y\beta} = d^2z/dt^2 = -R\omega^2\beta \sin\theta \quad (8)$$

$$a_{z\beta} = (d^2x/dt^2) \sin\theta - (d^2y/dt^2) \cos\theta = -R\omega^2 2\beta \sin\theta + l\omega^2 \quad (9)$$

where $a_{x\beta}$, $a_{y\beta}$, and $a_{z\beta}$ indicate the acceleration vectors acting along the corresponding coordinate axes.

Equations (7) to (9), thus obtained, serve as general formulae of acceleration generated by three types of synchronous planetary motion illustrated in FIG. 1, namely, type L, where $R = 0$;
type X, where $l = 0$; and
type L-X, where $l/R = +1$ or $-1$.

From these equations, the centrifugal force vectors (same magnitude with the acceleration acting in the opposite direction) at various points on the cylinder can be computed for the three types of planetary motion indicated immediately above.

Figure 5:
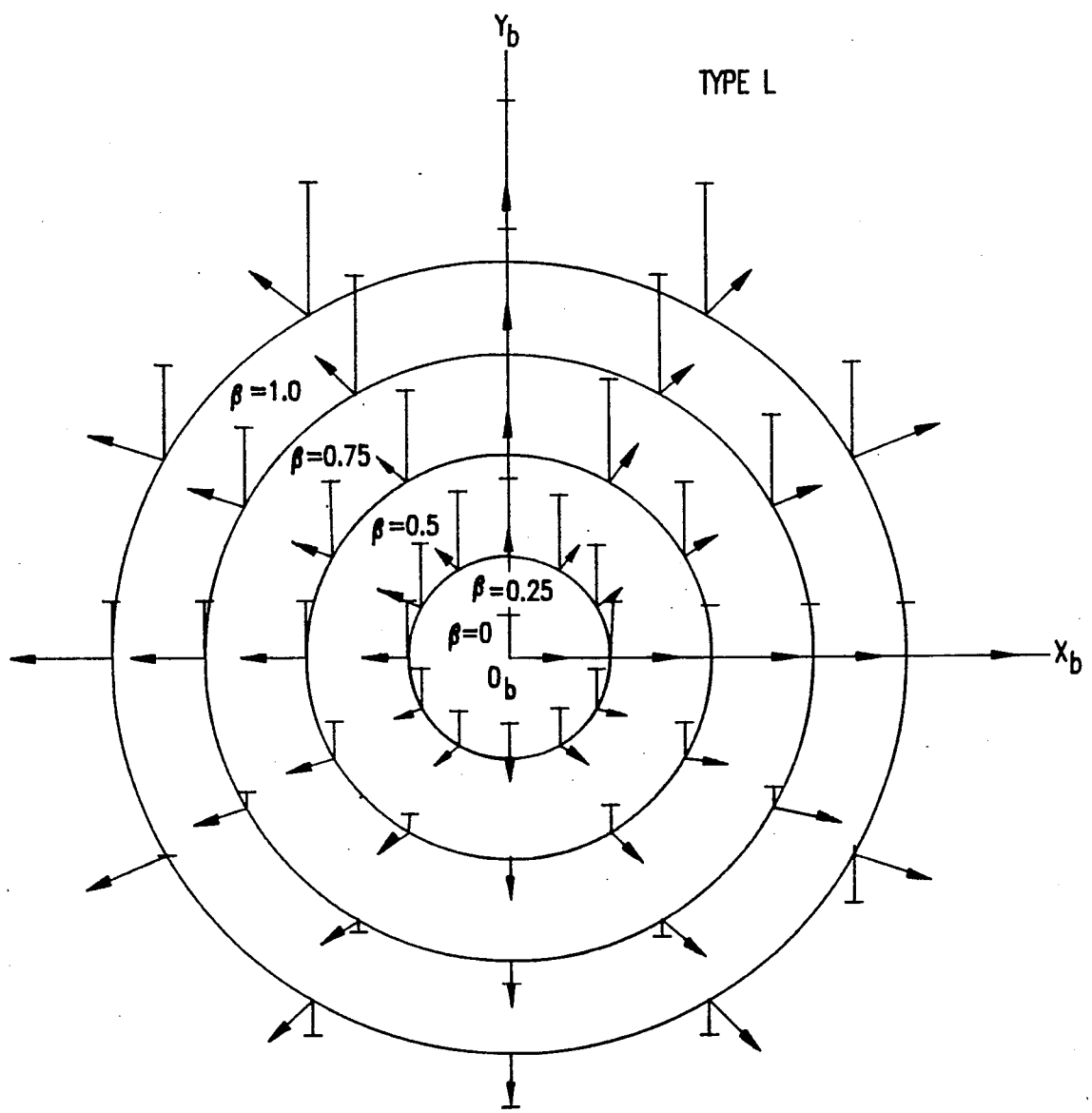
FIG. 5 is a force distribution diagram illustrating the force vectors arising during synchronous planetary motion of type L apparatus.
Figure 6:
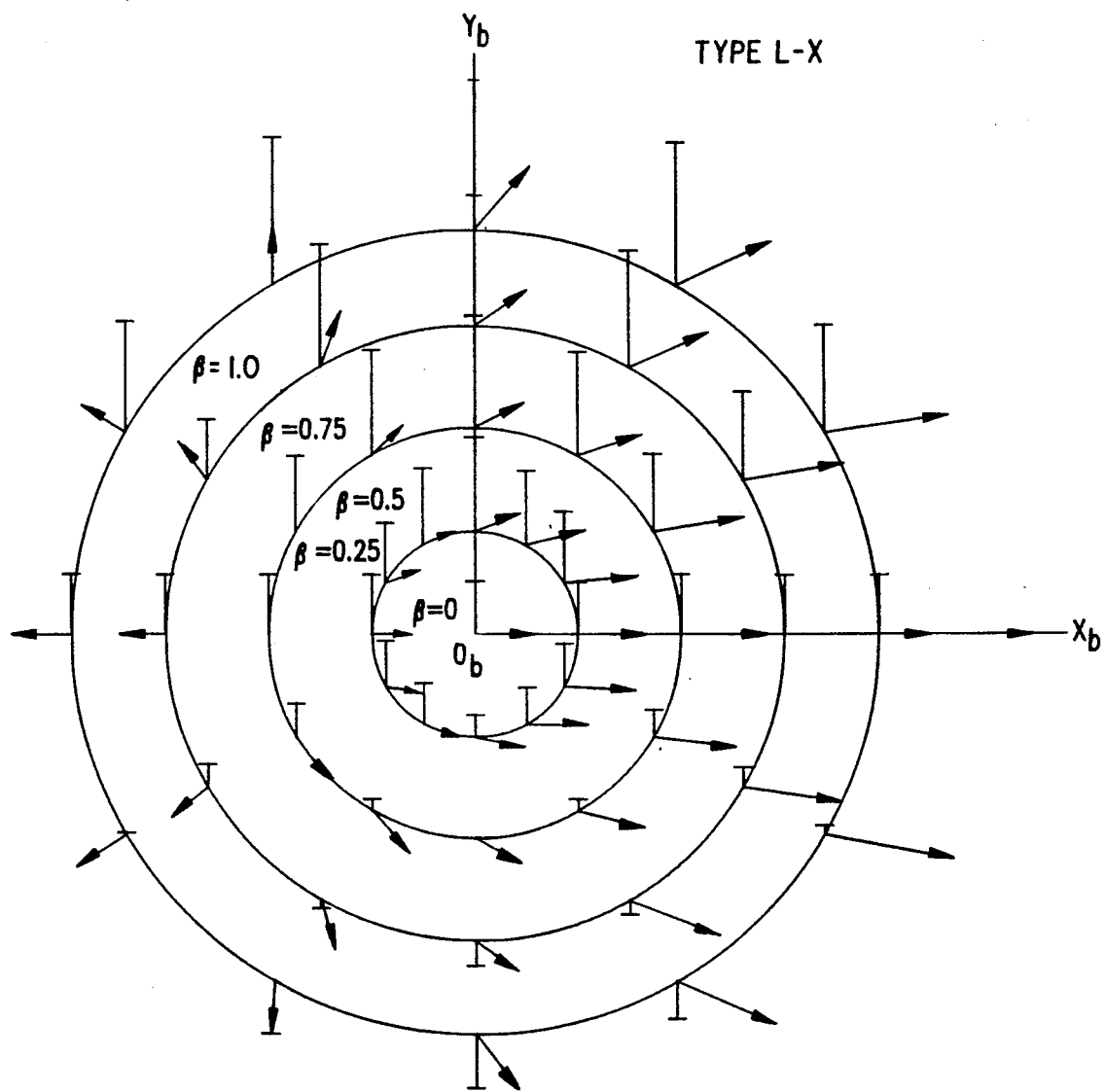
FIG. 6 is a force distribution diagram illustrating the force vectors arising during synchronous planetary motion of type L-X apparatus.
Figure 7:
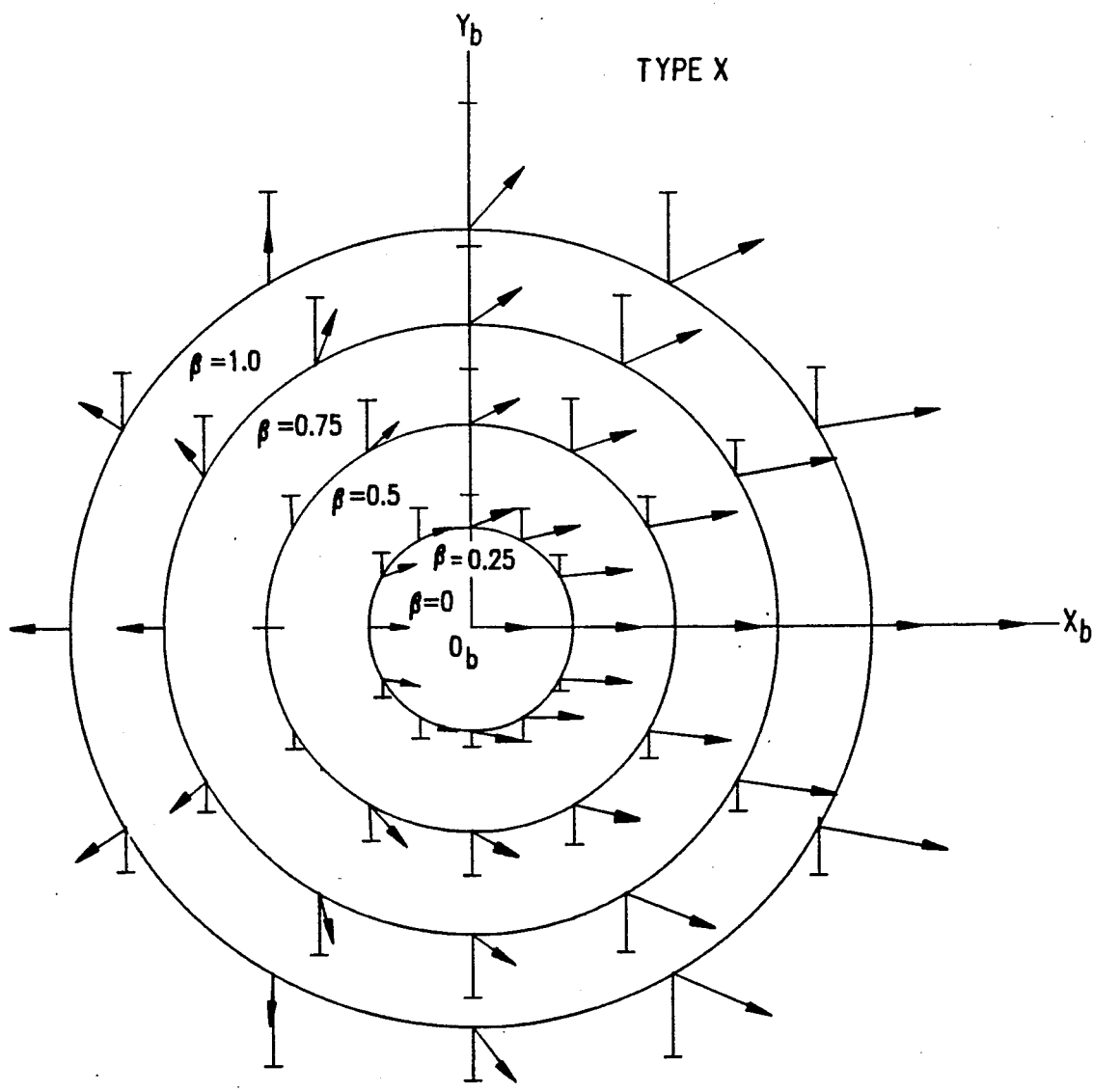
FIG. 7 is a force distribution diagram illustrating the force vectors arising during synchronous planetary motion of type X apparatus.

Such computations have been performed, and the results are shown diagrammatically in FIGS. 5-7, respectively. In order to express three-dimensional patterns of the centrifugal force vectors on a two dimensional diagram, the two force vectors, $a_{xb}$ and $a_{yb}$, are combined into a single arrow forming various angles from the $x_b$-axis, whereas the third force vector, $a_{zb}$, which acts perpendicularly to the $x_b$-$y_b$ plane, is drawn as a vertical column along the $y_b$-axis. The ascending column indicates the force acting upwardly ($z_b > 0$) and the descending column indicates the force acting downwardly ($z_b < 0$). Several concentric circles around point $O_b$ (the axis of the cylinder) indicate locations on the cylinder corresponding to the parameter $\beta$ or $\beta'$, where $\beta'$ is the ratio $r/l$ for type L planetary motion. The distribution of the centrifugal force vectors in each diagram is fixed to the $x_b$-$y_b$-$z_b$ body coordinate system and every point on the cylinder rotates around point $O_b$ ($x_b$-axis) in either a clockwise or a counterclockwise direction as determined by the planetary motion of the cylinder.

As shown in these diagrams, the arbitrary point on the cylinder is subjected to a highly complex three-dimensional fluctuation of the centrifugal force field which varies in both magnitude and direction during each revolutional cycle.

The force distribution patterns also change with the location of the point on the cylinder where force vectors tend to increase their magnitude in the remote location from the axis of the cylinder. Each planetary motion generates a characteristic distribution of the centrifugal force vectors. For example, the type L planetary motion (FIG. 5) forms a symmetrical distribution of outwardly radiating arrows around all circles and an asymmetric distribution of columns along the $y_b$-axis on the diagram, while the type X planetary motion (FIG. 7) forms a pattern of the force distribution which consists of an asymmetric distribution of arrows along the $x_b$-axis and a symmetric distribution of columns around point $O_b$. In contrast to these patterns, the hybrid type L-X planetary motion (FIG. 6) exhibits asymmetric distributions of both arrows and columns, with each distribution being identical to that of the "parent" from which it is derived.

FIGS. 3A and B illustrate an embodiment of a cross-axis coil synchronous flow-through planet centrifuge which was constructed in accordance with the present invention.

Referring first to FIGS. 3A and 3B, the apparatus shown includes a rotary frame 100 having an axis of revolution defined by the central shaft 2, and including an assemblage of inner side plates 3,3, outer side plates 4,4, an upper plate 5 and a lower plate 6, all rigidly connected together. A motor 1 is preferably supported below the housing in which the assemblage of plates is located, and is adapted for reversibly driving the assemblage in revolution about the central shaft 2. Coil holder shafts 7a, 7b are horizontally supported by the inner and outer side plates, and are disposed symmetrically on each side of the rotary frame at a distance of about 10 cm from the central shaft of the centrifuge. A pair of identically shaped coil holders 8a,8b is mounted on a respective one of each of the holder shafts. Each of the coil holders is symmetrically positioned relative to the central shaft on each side of the rotary frame between a respective pair of inner and the outer side plates. Preferably, the coil holders are located on opposite sides of the central axis of the centrifuge at a distance of about 12.5 cm from the center of the holder shaft, as viewed in FIG. 3B. As also shown in FIG. 3B, the coil holders 8a, 8b are offset from the central shaft 2 such that any radius extending from the central shaft 2 to the axis within each coil holder 8a or 8b is non-perpendicular to the axis within the respective coil holder.

The planetary motion of each coil holder is accomplished by providing a set of miter gears and toothed pulleys. In particular, as seen in the Figures, the apparatus includes a first stationary miter gear 9 rigidly above the bottom plate of the centrifuge centrally about the central shaft 2. The stationary "sun" gear is coupled to a pair of identical "planetary" gears 10a,10b. The planetary gears are each attached to an "inner end" of a countershaft 11a, 11b, which extends from the central shaft radially of the rotary frame and outwardly toward the periphery of the rotary frame through the lower portion of a respective inner side plate. This gearing arrangement produces synchronous rotation of each countershaft during simultaneous revolving motion of the rotary frame. The rotation of the countershafts is imparted to the coil holders via toothed pulleys 12a, 12b, which are mounted at the "outer end" of a respective countershaft, and which are coupled to similar toothed pulleys 13a, 13b supported for rotation about a respective coil holder shaft 7a, 7b at the center of the respective coil holder.

The apparatus in the Figures can be constructed so that instead of a second coil holder 8b mounted on coil holder shaft 7b, a balancing counterweight (not shown) is provided.

Various experiments were conducted using the apparatus described above, and the experiments, as well as their results, are discussed below. In the course of conducting these experiments, minor modifications were made to the embodiments of the invention used which did not change the structure of the apparatus in any material manner.

For example, the material chosen for the side plates and the upper and lower plates was aluminum because it enhanced the obtention of results; however, it is to be understood that any material which does not unduly burden the operation of the apparatus by virtue of its weight or wear characteristics may be used. In addition, flow tubes 17b from the coil holders were passed through guide rings 17c attached to the respective outer side plate 4a or 4b. The flow tubes then were led to a side hole in the central shaft 2 whereafter they exited the centrifuge through a stationary guide pipe projecting downwardly from the top plate of the centrifuge. Near the exit hole, each flow tube was firmly held by a clamp equipped with a silicone rubber pad. The flow tubes were then lubricated with grease and protected by a piece of tygon tubing to prevent direct contact with metal parts. Normally, with proper care, the flow tubes can maintain their function for many months of operation.

The three miter gears used in the apparatus of the present invention cooperate together to provide synchronous planetary motion of the two coil holders, or of the coil holder and the counterweight. The three gears ar all preferably identical in shape and are all preferably of the type commonly referred to as a "45°" miter gear. Preferably, the sun gear is a plastic gear, while the other planetary gears, which make contact with and ride on the sun gear, are provided as steel gears.

The revolutional speed of the apparatus was regulated in a range between 0 rpm and 1000 rpm in either direction at high stability by a speed control unit (available through Bodine Electric Company, Chicago, Ill.). A plastic baffle placed close to the rotary frame around the periphery of the centrifuge was found to reduce windage resuting in a reduction of the torque by over 30% at the maximum speed of 500 rpm.

In order to apply various types of column holders in the same apparatus, both the column holder and the counterweight holder are designed such that they can be easily removed from the rotary frame simply by loosening a pair of screws on each bearing block. This design also facilitates mounting of the coiled column on the column holder and determining a proper counterweight mass to be applied for balancing the centrifuge system.

EXPERIMENTS CARRIED OUT WITH THE FOREGOING APPARATUS

In using the above-described apparatus, two sets of column holders were fabricated. The first set included long spool-shaped holders measuring about 25 cm between the flanges with different hub diameters ranging from 5 cm to 25 cm. Each holder was paired with an appropriate counterweight mass mounted on a counterweight holder. These column holders were used to measure stationary phase retention and partition efficiency in short coils mounted at two different locations on the holder, i.e., at the center and at 10 cm left from center. The second set of holders included a pair of identical spool-shaped holders each measuring 5 cm between the flanges and 15 cm in hub diameter. These holders were used exclusively for mounting long multilayer coils suitable for large-scale preparative separations, and were symmetrically mounted on both sides of the rotary frame to effect perfect balancing of the centrifuge system without the use of a counterweight (see FIGS. 3A and 3B). In using the holders of this second set, two columns were connected in series with a transfer tube, or alternatively, each of the columns were used separately.

The organic solvents used for preparation of two-phase solvent systems included n-hexane, ethyl acetate, chloroform, n-butanol, sec.-butanol, methanol, and acetic acid. Among these solvents, acetic acid was reagent grade and was obtained from J. T. Baker Chemical Co., Phillipsburg, N.J. All other solvents were glass-distilled chromatographic grade and purchased from Burdick and Jackson Laboratories, Inc., Muskegon, Mich.

Using the above solvents, the following nine (9) volatile two-phase solvent systems were prepared:
(1) n-hexane/water;
(2) n-hexane/methanol;
(3) ethyl acetate/water;
(4) ethyl acetate/acetic acid/water (4:1:4);
(5) chloroform/water;
(6) chloroform/acetic acid/water (2:2:1);
(7) n-butanol/water;
(8) n-butanol/acetic acid/water (4:1:5); and
(9) sec.-butanol/water.

Each solvent mixture was thoroughly equilibrated in a separatory funnel at room temperature by repeated shaking and degassing, and separated before use.

The experiments performed were done so with short coils prepared from tubing having a length of 2-3 meters and an internal diameter of 2.6 mm. The tubing used was made of polytetrafluoroethylene (PTFE tubing) available from Zeus Industrial Products, Raritan, N.J. The tubing was wound into coils coaxially around holders of 5 cm, 15 cm and 25 cm hub diameters. For each holder the coil was mounted at two different locations; one at the center of the holder (l=0 cm) and the other at 10 cm left of the center of the holder (l=−10 cm). Although right-handed coils were mainly used for the experiments performed with the above-described apparatus, left-handed coils were also tested at l=−10 cm on the 25 cm diameter holder. These columns were firmly held on the holder with several pieces of fiberglass reinforced adhesive tape.

Each end of the coil was directly connected to a flow tube with 0.85 mm i.d. and 1 meter in length, without the sude of a bulky commercial adaptor which would distort the helical configuration near the junction. The connection was made by using short pieces of intermediate size PTFE tubing.

Measurements of Stationary Phase Retention

Experiments were performed according to a procedure in which, for each coil, retention was measured for the nine pairs of two-phase solvent systems enumerated above.

For each measurement, the coil was first entirely filled with the stationary phase. Then the apparatus was run at a desired revolutional speed while the mobile phase was pumped through the coil at 120 ml/h with a Chromatronix Cheminert Pump. The effluent from the outlet of the coil was collected in a 25 ml capacity graduated cylinder to measure the volume of the stationary phase eluted from the coil as well as the total volume of the mobile phase eluted. During the run, the temperature inside the centrifuge was controlled within a range of 21-23 degrees Centigrade by placing an ice bag directly over the top plate of the centrifuge. The run was continued for 10 minutes or slightly longer so that the effluent volume exceeded the total capacity of the coil. Thereafter, the apparatus was stopped and the coil was emptied by connecting the inlet of the coil to an $N_2$ gas line pressurized at about 80 psi. The coil was then flushed with several milliliters of methanol miscible with both phases. Finally, the coil was once again flushed with several milliliters of the stationary phase to be used in the next experiment. During emptying and flushing of the coil with $N_2$, the apparatus was rotated at a moderate speed of about 100–200 rpm in a direction making the coil outlet the head to promote the drainage of the column contents.

Figure 8:
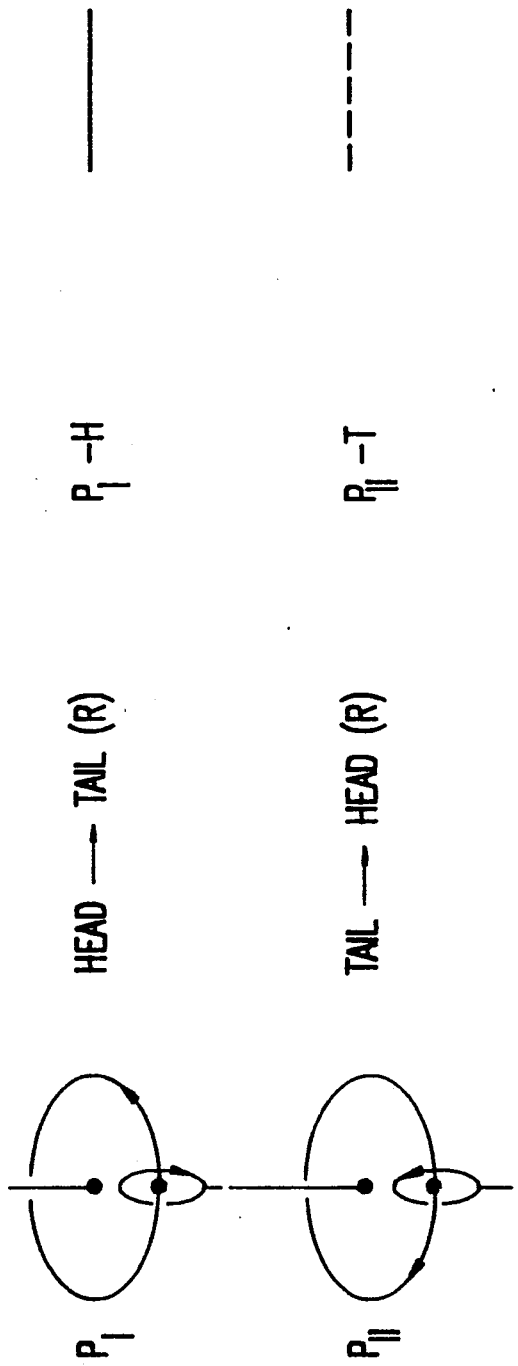
FIG. 8 illustrates two elution modes at the central coil position.

In experiments where the coils were mounted at the center of the coil holder, the measurements were mainly performed in two elution modes as shown in FIG. 8, each at four different revolutional speed of 200 rpm, 300 rpm, 400 rpm and 500 rpm. In each case, both upper and lower phases were used as the mobile phase in each solvent system. The coils mounted at 10 cm left from the center of the holder, where the laterally acting Coriolis force field becomes asymmetric, produced several levels of stationary phase retention according to the direction of the planetary motion and handedness of the coil as well as the head-tail elution mode. Thus a total of eight combinations were tested with the 25 cm diameter holder at 500 rpm by the use of both right-handed and left-handed coils each mounted at 10 cm from the center of the holder (see FIG. 9). In the remaining cases, the measurements were limited to four combinations with the right-handed coils at 500 rpm. Any experimental condition which produced a significant degree of retention at 500 rpm was further examined under reduced revolutional speeds of 400 rpm, 300 rpm and 200 rpm to obtain phase distribution diagrams (to be described below).

Phase Distribution Diagrams

As a result of the foregoing experiments, it was found that retention of the stationary phase could be correlated as a percentage of the total column capacity in accordance with the expression:

$$100 \; (V_c + V_f - V_s) / V_c,$$

where
$V_c$ denotes the total capacity of the coil;
$V_f$ denotes the free space in the flow tubes; and
$V_s$ denotes the volume of the stationary phase eluted from the coil.

Using the retention data thus obtained, the hydrodynamic distribution of the two solvent phases in the coil was summarized in a phase distribution diagram which was constructed by plotting percentage retention of the stationary phase as a function of revolutional speed for each mobile phase. A group of retention curves produced by different elution modes but otherwise identical experimental conditions can be illustrated in the same diagram. In order to distinguish each elution mode in the phase distribution diagram, a set of symbolic designs was used to draw phase distribution curves as illustrated in FIGS. 8 and 9.

As a result of the experiments performed, it was found that the degree of stationary phase retention could be quite different between the two locations on the same holder. Moreover, it was found that in the lateral coil position, retention of the stationary phase could be significantly affected by the direction of the planetary motion as well as the head-tail elution modes.

A. Phase Distribution Diagrams Obtained from Central Coil Position (l=0 cm)

Figure 10A:
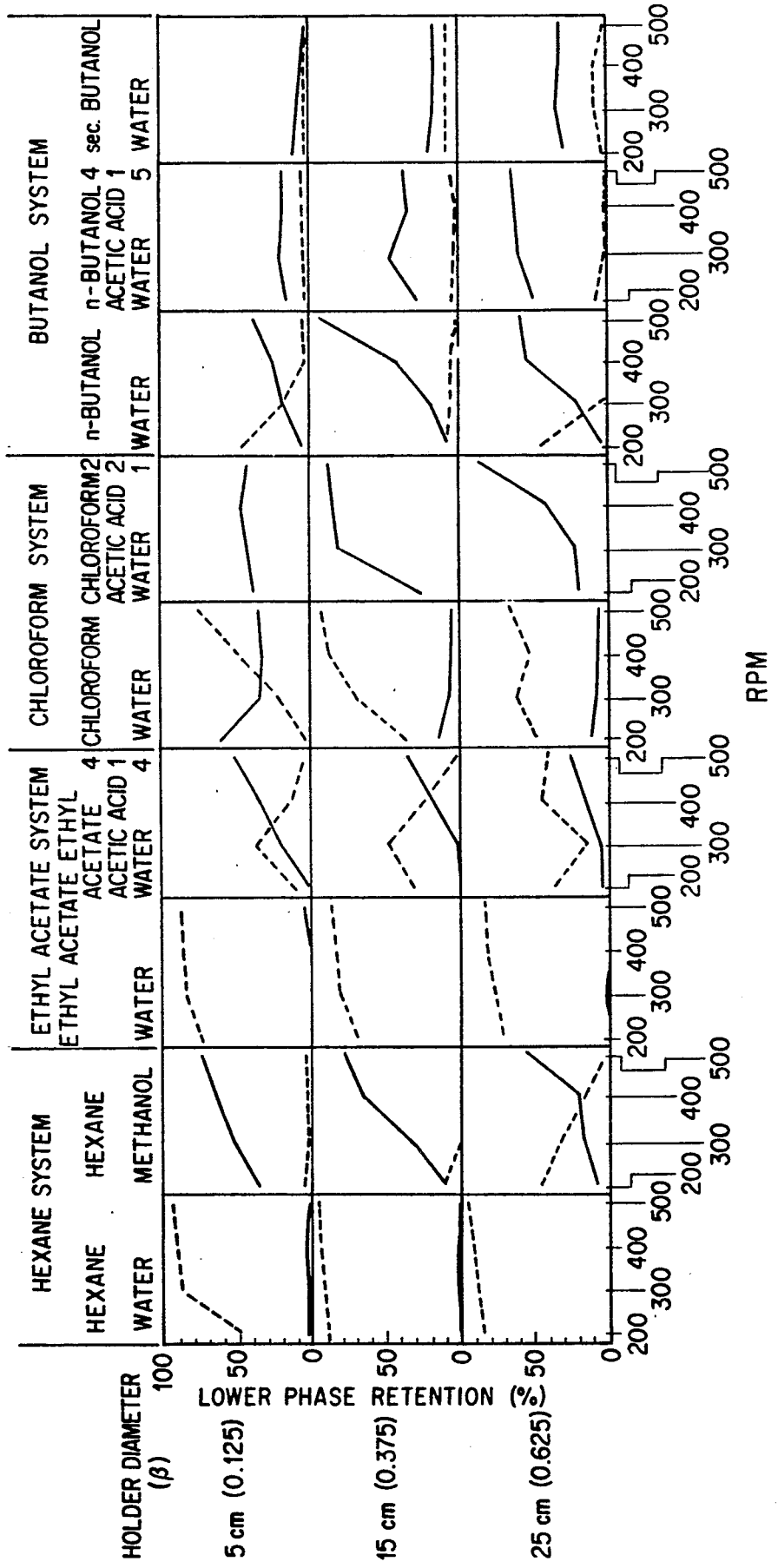
FIGS. 10A and 10B are a series of phase distribution diagrams at the central position.
Figure 10B:
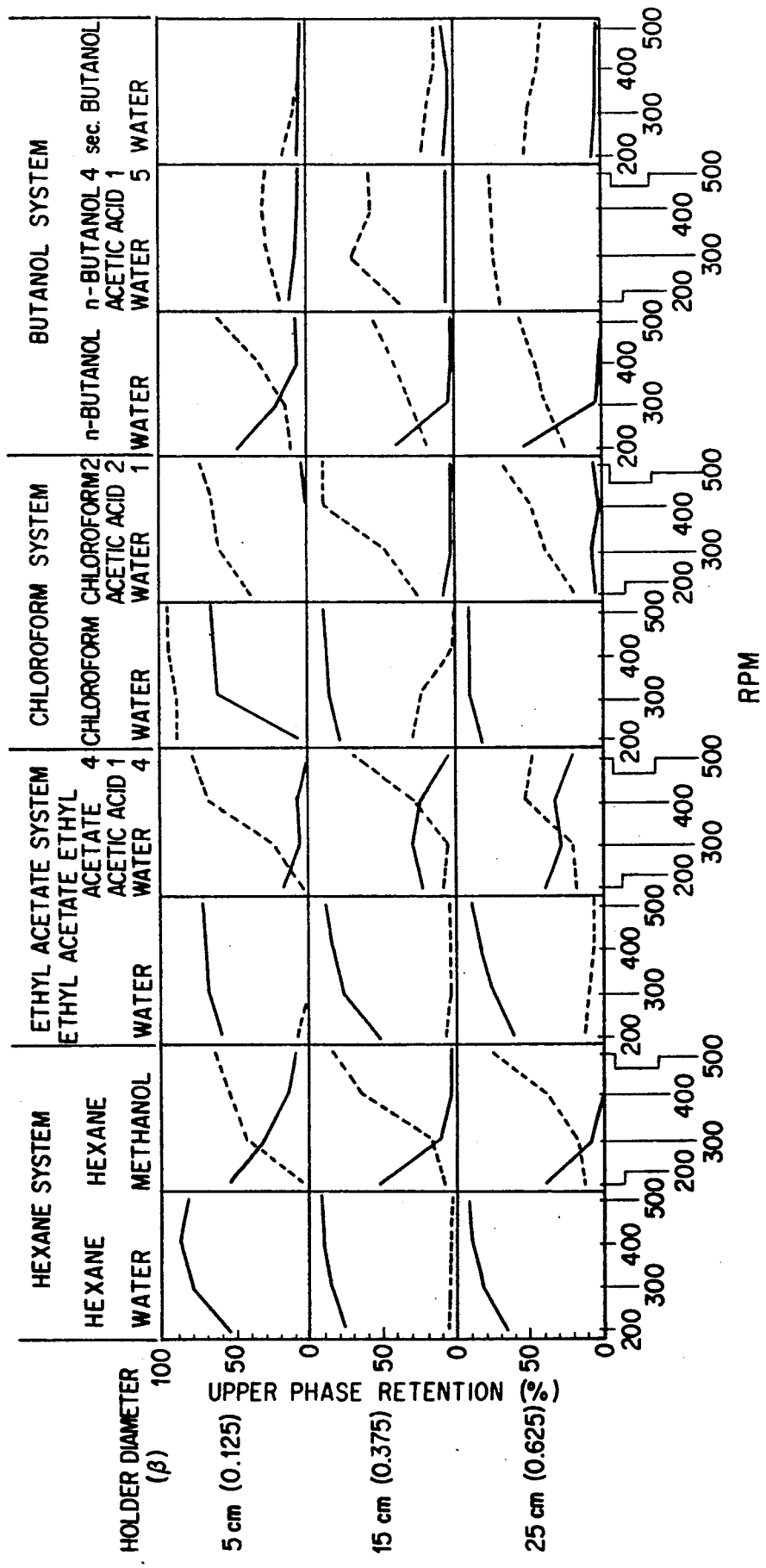

Referring to FIG. 10, there are shown the results of phase retention studies obtained from the central coil position. Each column in the Figure consists of phase distribution diagrams obtained from the same solvent system (labelled at the top of the column). The columns are arranged from left to right in the order of the hydrophobicity of the major organic solvents, i.e., n-hexane, ethyl acetate, chloroform, n-butanol, and sec.-butanol. As indicated on the left margin of the diagrams, the top three rows show retention of the lower phase obtained by elution with the upper phase, and the bottom three rows show retention of the upper phase by elution with the lower phase. Within each mobile phase group, the first row was obtained from the 5 cm diameter coil (or at $\beta=0.125$), the second row was obtained from the 15 cm diameter coil (at $\beta=0.375$), and the third row from the 25 cm diameter coil (i.e., at $\beta=0.625$), where $\beta$ is the ratio of the radius of rotation (the distance from the central axis of the holder to the coil) to the radius of revolution (the distance from the central axis of the centrifuge to the axis of the holder). $\beta$ determines both the magnitude and the direction of the centrifuge force field acting on the various locations of the holder. Two retention curves in each diagram were obtained from different elution modes: the solid curve indicating the head-to-tail elution mode, and the broken curve indicating the tail to head elution mode.

Phase distribution diagrams obtained from the central coil position share common features with those from the original cross-axis CPC with a 10 cm revolutional radius and may be similarly divided into three categories according to the hydrophobicity of the solvent systems.

Hydrophobic binary solvent systems characterized by high interfacial tension between the two phases, including hexane/water, ethyl acetate/water, and chloroform/water, show high retention when the upper phase is eluted from the tail toward the head (broken curves in the upper column) or the lower phase from the tail toward the head (broken curves in the lower column). On the other hand, hydrophilic solvent systems associated with low interfacial tension, such as n-butanol/acetic acid/water (4:1:5) and sec.-butanol/water, display an opposite hydrodynamic trend, giving better retention by eluting either the upper phase from the head toward the tail (solid curves in the upper column) or the lower phase from the tail toward the head (broken curves in the lower column). The rest of the solvent systems with intermediate degrees of hydrophobicity generally show a hydrodynamic trend similar to that of the hydrophilic solvent systems but mostly yield much higher retention level. In both hydrophilic and intermediate solvent systems, the retention is sensively affected by the $\beta$ values. In the hydrophilic solvent group the retention is substantially improved at greater $\beta$ values whereas retention of the intermediate solvent systems changes with the $\beta$ values in various ways. Hexane/methanol gives higher retention at small $\beta$ values while chloroform/acetic acid/water (2:2:1) shows highest retention at the moderate $\beta$ value of 0.375.

The overall results obtained with the central coil position indicate that, compared with the original X-axis CPC operated at 200–800 rpm, the present system yields somewhat lower retention for intermediate solvent systems but substantially improved retention of hydrophilic solvent systems at large $\beta$ values.

B. Phase Distribution Diagrams Obtained from Lateral Coil Position (l= −10 cm)

Figure 11A:
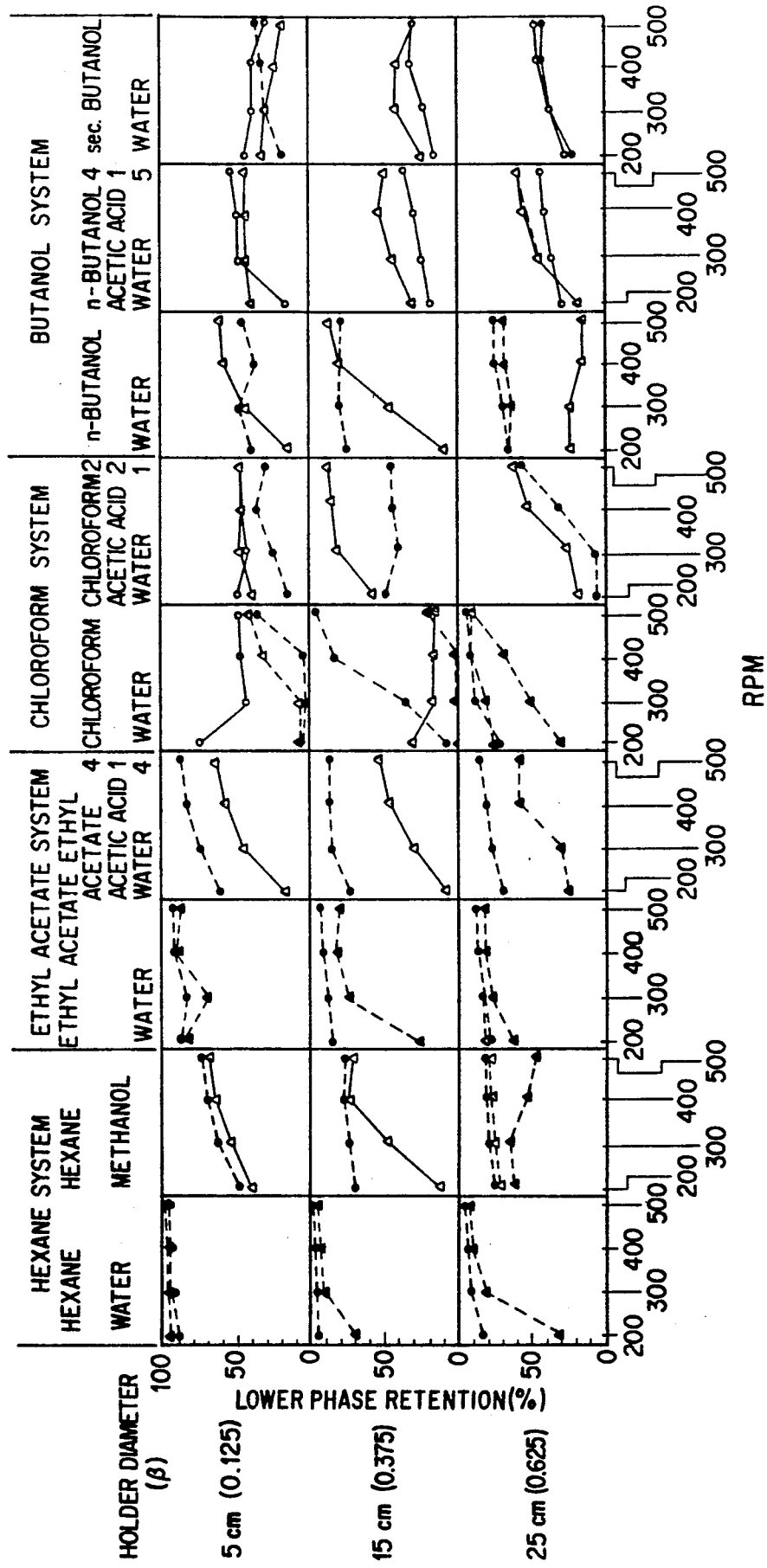
FIGS. 11A and 11B are a series of phase distribution diagrams at the lateral position.
Figure 11B:
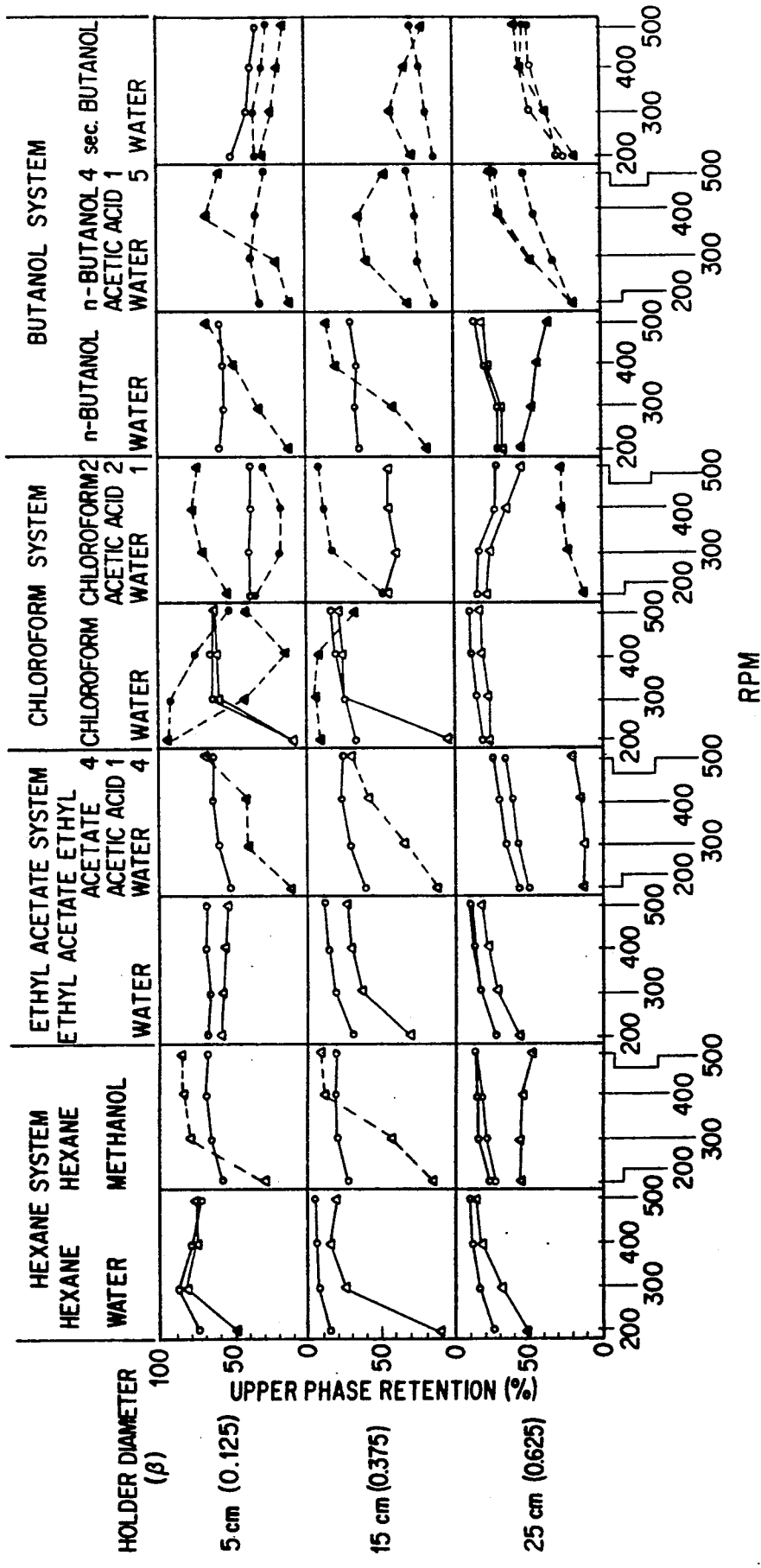

A set of phase distribution diagrams obtained from the coil mounted at 10 cm left from the center of the holder is illustrated in FIG. 11.

As briefly mentioned earlier, the coil mounted at a lateral location is subjected to an asymmetric Coriolis force field between the upper and the lower halves of the rotating holder, thus causing different levels of retention according to the combination of direction of the planetary motion and elution modes of the mobile phase. There are eight possible combinations as summarized in FIG. 9. Planetary motion $P_I$ is identical to the motion of the disc shown in FIG. 2, while $P_{II}$ is the reversed motion resulting in both rotation and revolution of the holder being reversed. In each planetary motion, the mobile phase can be eluted in either the head to tail or the tail to head mode, thus yielding four different combinations. For each of these four combinations, there is a choice of elution in either inward or outward direction which requires the use of both right-handed and left-handed coils. Consequently, the total eight experimental conditions are possible for each solvent systems. FIG. 9 also shows a set of symbolic designs which were used to distinguish phase distribution curves obtained from different experimental conditions.

All eight combinations were first examined with the 25 cm diameter holder ($\beta = 0.625$) at 500 rpm (FIG. 12) and among those the three combinations for the best retention were further tested at various revolutional speeds to draw phase distribution curves as shown in FIG. 11 (bottom row in each mobile phase group). These data clearly indicated that the choice of inward-outward elution modes gives little effect on the retention. Therefore, the rest of the studies on the 15 cm and 5 cm diameter holders were performed exclusively with the right-handed coils to investigate the effects of the two other parameters, i.e., the planetary motion and the head-tail elution mode. All four combinations possible with the right-handed coils were tested at 500 rpm and two or more combinations which produced significant retention values were further studied with lower rpms to obtain phase distribution curves (FIG. 11).

The overall results of the retention studies on the lateral coil position revealed remarkable improvement of retention over those obtained from the central coil position for almost all solvent systems. Intermediate solvent systems such as hexane/methanol, ethyl acetate/acetic acid/water (4:1:4) and n-butanol/water produced excellent retention in all $\beta$ values with the proper elution mode. Great improvement in retention is also observed in hydrophilic solvent systems which are extremely useful for separations of polar compounds. Retention of n-butanol/acetic acid/water (4:1:5) exceeds 50% level in all $\beta$ values while that of sec.-butanol/water reaches 50% at $\beta = 0.625$. Although chloroform solvent systems failed to show substantial improvement in retention, they give satisfactory retention between the $\beta$ values of 0.375 and 0.625 with the highest retention around $\beta = 0.375$. The above results clearly indicate that the lateral coil position permits satisfactory retention of the stationary phase in all solvent systems examined, provided that the proper combination of planetary motion and head-tail elution mode is chosen.

Figure 13B:
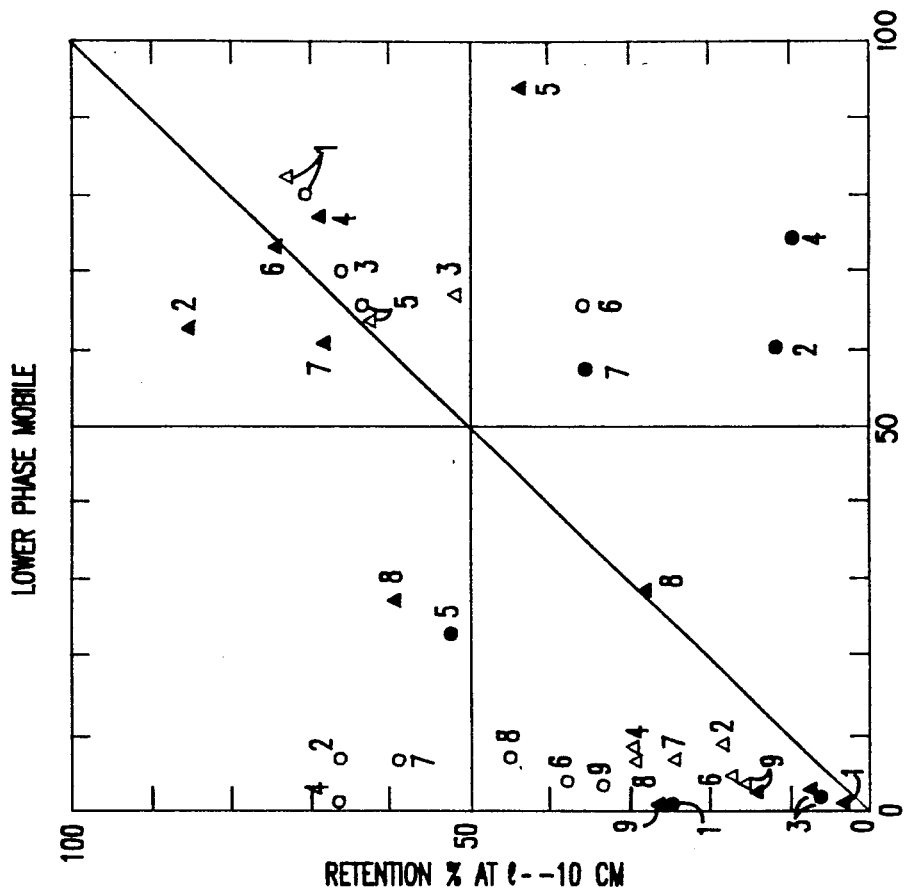
FIGS. 13A and 13B illustrate stationary phase retention in short coils for $\beta = 0.125$, 5 cm holder.
Figure 13A:
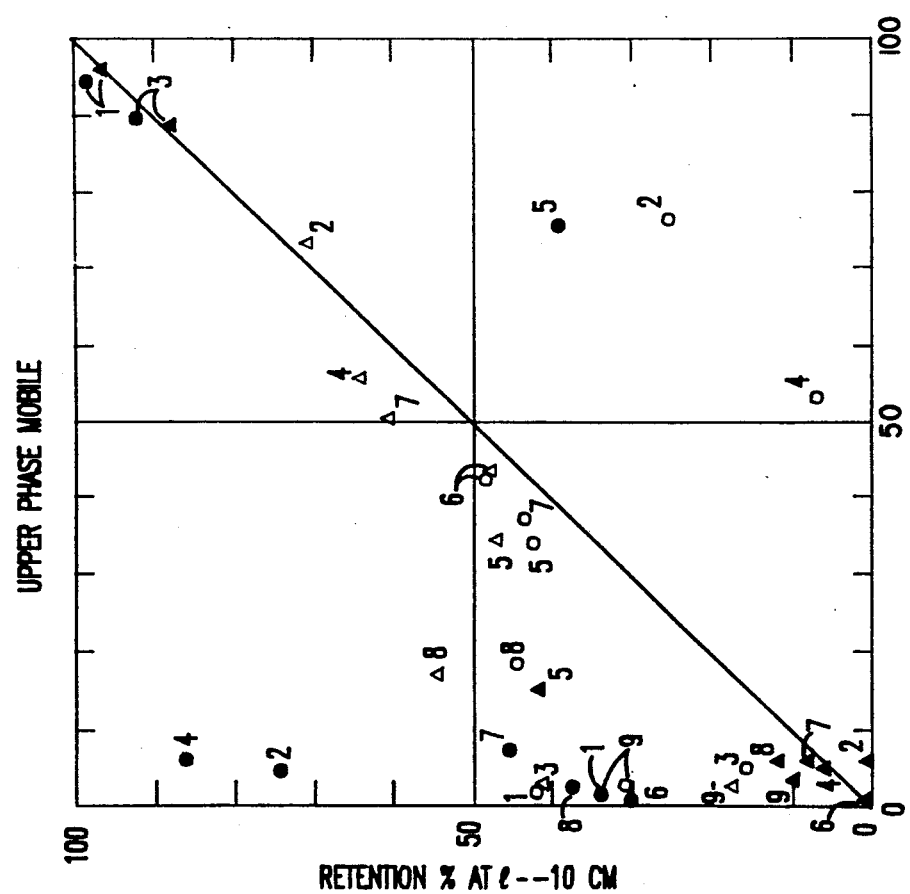
Figure 14B:
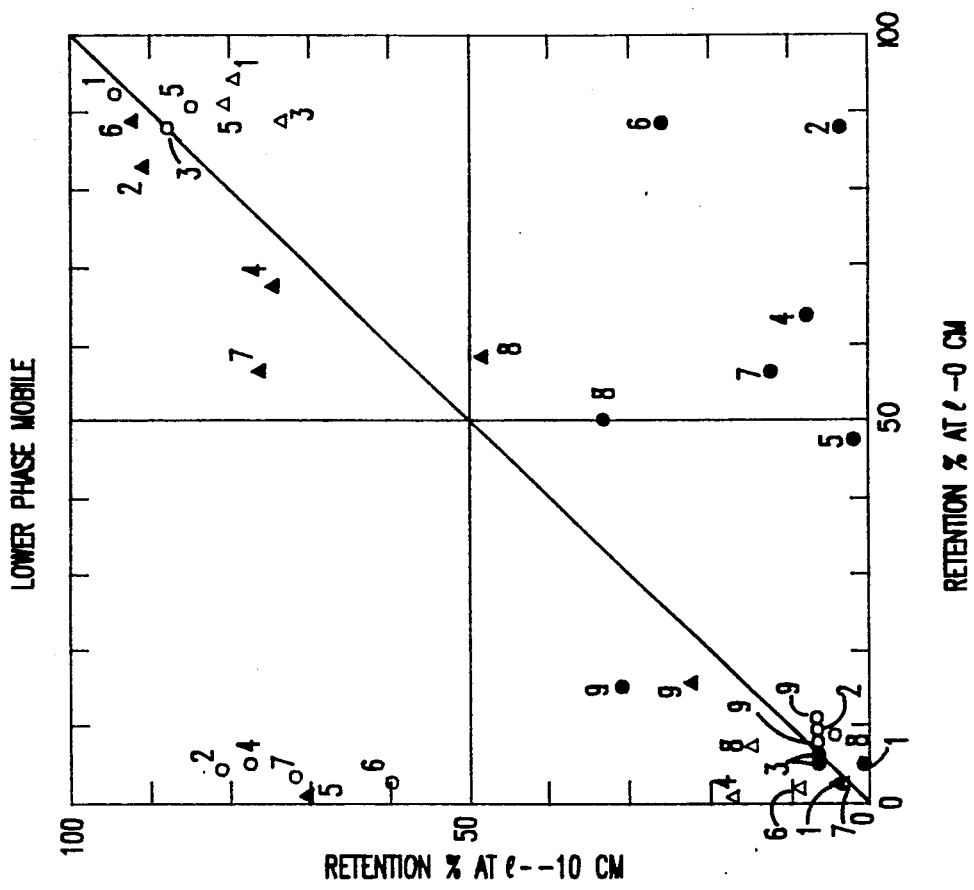
FIGS. 14A and 14B illustrate stationary phase retention in short coils for $\beta = 0.375$, 15 cm holder.
Figure 14A:
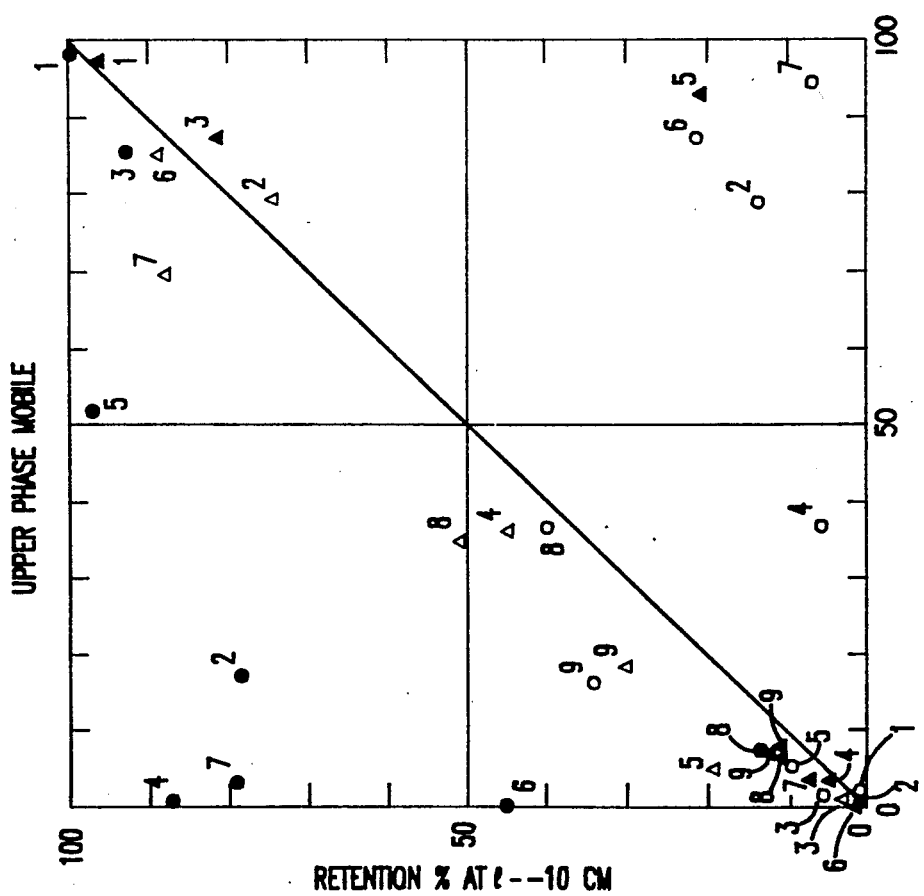

Retention data obtained from the two coil positions on each holder can be more conveniently compared in each mobile phase if expressed in a single diagram as shown in FIGS. 13-15. In each diagram, the abscissa indicates the retention values obtained at the central coil position at 500 rpm and the ordinate, those obtained at the lateral coil position under otherwise identical experimental conditions. Each data point is marked with a specific symbol assigned for the applied experimental condition (planetary motion and head-tail elution mode) as indicated in FIG. 9. In order to specify the applied solvent systems, these points are individually labelled 1 through 9, each number corresponding to a particular two-phase solvent system as specified under the figure caption.

A diagonal drawn in each diagram divides the whole area into two equal parts, the area above the line indicates the improved retention for the lateral position and that below the line, lowered retention. The longer the distance of the point from the diagonal, the greater the effect on retention. The diagram is also divided evenly into four small squares by thin lines, each square having specific implication: The upper left and lower right squares represent satisfactory retention of over 50% in the lateral coil ($l = -10$ cm) and in the centered coil ($l = 0$ cm), respectively, while the upper right square provides satisfactory retention for both coils and the lower left square, unsatisfactory retention for either coil. Further, if the upper right square contains two different symbols with the same color and the same number, satisfactory retention is provided in the coil mounted throughout the width of the holder ($-10$ cm $< l <$ 10 cm), while the same is observed in the upper left square, satisfactory retention is limited to both left and right lateral positions excluding the central part of the holder ($l = -10$ cm and 10 cm).

While the above indication for applicability of the coil positions can also be extracted from FIGS. 10-12 without much difficulty, these diagrams further furnish invaluable information by disclosing a peculiar hydrodynamic effects associated with the lateral coil position. For example, in FIG. 14 ($\beta = 0.375$) solid circles (tail to head elution under planetary motion $P_I$) and open triangles (head to tail elution under planetary motion $P_{II}$) dominate above the diagonal, if the upper phase is mobile (left), whereas open circles (head to tail elution under planetary motion $P_I$) and solid triangles (tail to head elution under planetary motion $P_{II}$) dominate above the diagonal, if the lower phase is mobile (right). These findings strongly suggest that the direction of the planetary motion is in some way closely related to the head-tail elution mode to govern the hydrodynamics in the lateral coil position, thus providing an important clue for speculation on the hydrodynamic mechanism associated with the X-axis CPC as discussed in the following.

HYDRODYNAMIC EFFECTS OF L-X PLANETARY MOTION

Figure 16A:
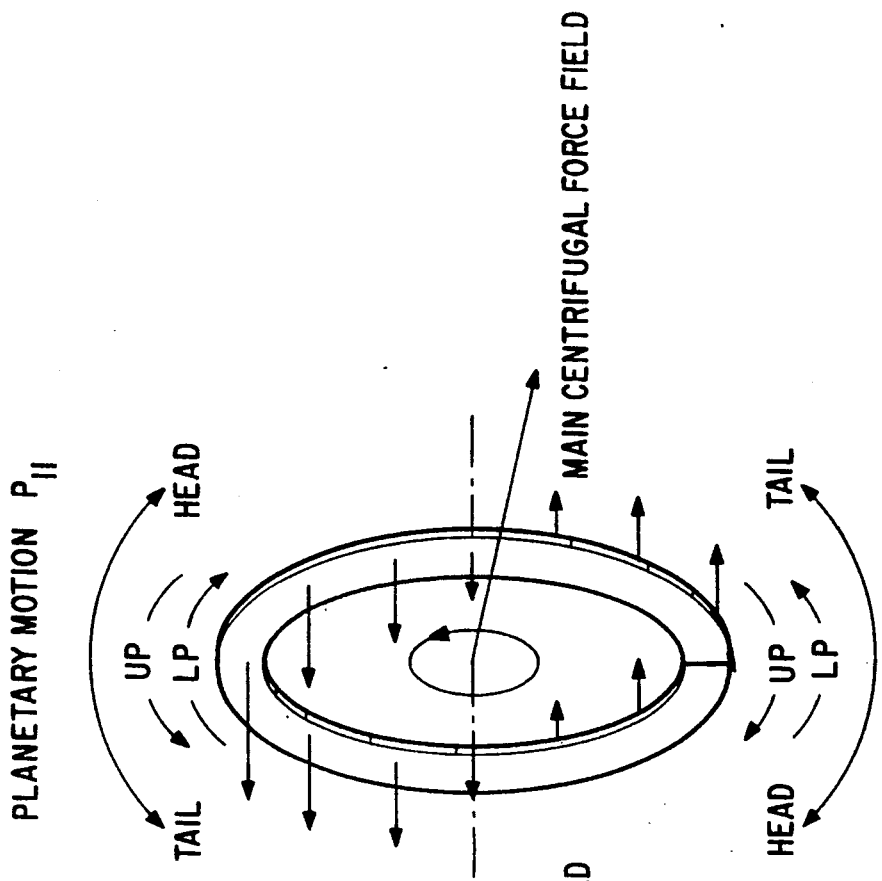
FIGS. 16A and 16B illustrates coils at the lateral position undergoing planetary rotation.
Figure 16B:
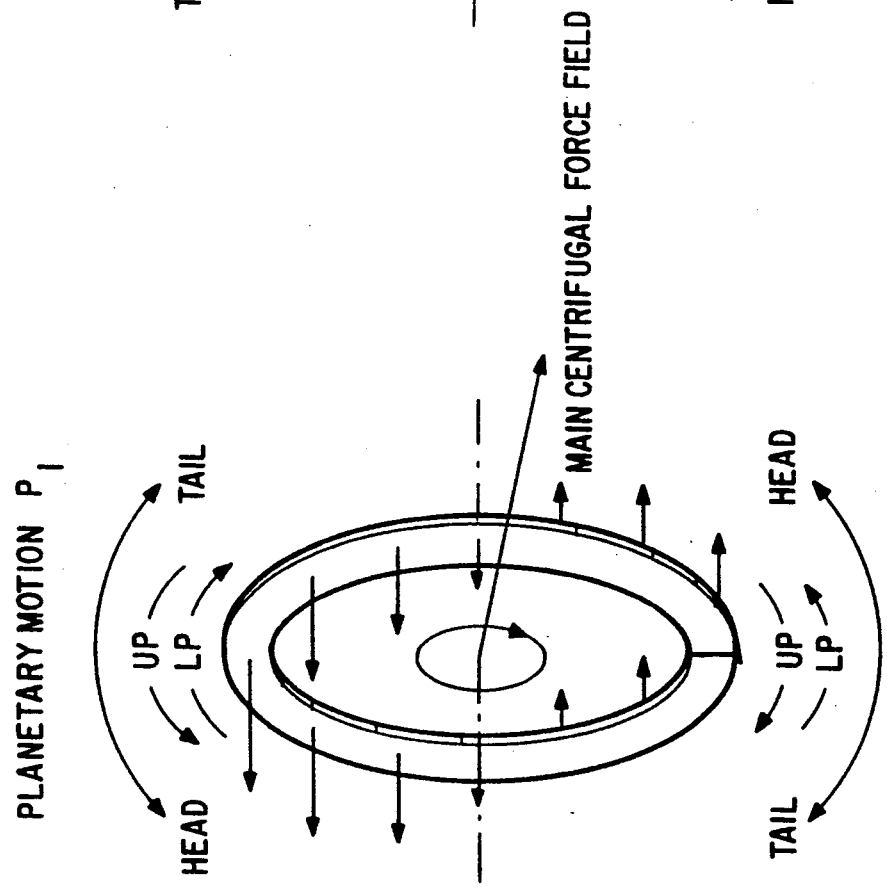

FIGS. 16A and 16B illustrate coils at the lateral position on the holders while undergoing planetary motion. FIG. 16A shows a first mode of planetary motion, while FIG. 16B shows a second mode of planetary motion. Because rotation and revolution are simultaneously reversed, these two planetary motions produce the identical Coriolis force field while reversed rotation of the holder causes reversal of the head-tail orientation of the coil. Under the main centrifugal force field directed radially toward the right as indicated by a large arrow, the upper (lighter) phase is driven toward the left and the lower (heavier) phase is driven toward the right in major portions of the coil.

In FIG. 16A, planetary motion PI determines the coil rotation, and hence the head-tail orientation of the coil as indicated by the pair of curved arrows at the top and the bottom of the diagram. Due to the asymmetric Coriolis force field between the upper and the lower halves of the coil, the countercurrent movement of the two solvent phases is accelerated in the upper portion of the coil due to suppressed emulsification while the movement is decelerated in the lower portion of the coil due to enhanced emulsification. Consequently, in this situation, the tail to head elution of the upper phase, and the head to tail elution of the lower phase (solid circles and open circles, respectively, in FIG. 14) result in enhanced retention of the stationary phase.

In FIG. 16B, planetary motion PII reverses both the rotation and the head-tail orientation of the coil, as illustrated. Due to the asymmetric Coriolis force field left unaltered, the countercurrent movement of the two solvent phases is similarly accelerated on the upper portion of the coil and decelerated in the lower portion of the coil. Therefore, in this case, the head-to-tail elution of the upper phase and the tail-to-head elution of the lower phase (open triangles and solid triangles, respectively, in FIG. 14) result in enhanced retention of the stationary phase.

In the 25 cm diameter holder ($\beta=0.625$), the hydrodynamic effects on the lateral coil position are substantially modified as seen in FIG. 15 where solid symbols dominate above the diagonal in the left diagram (enhanced head-to-tail movement of the upper phase) and open symbols dominate in the right diagram (enhanced head-to-tail movement of the lower phase. This may be caused by the Coriolis force field acting on the proximal and distal portions of the coil to alter hydrodynamic trend of the two solvent phases to promote tail-to-head movement of the upper phase and tail-to head movement of the lower phase. On a large diameter holder, this effect may overcome that of the asymmetric Coriolis force field acting on the upper and the lower sides of the coil. The latter effects, however, are still evident within each elution mode for each solvent system.

Figure 17:
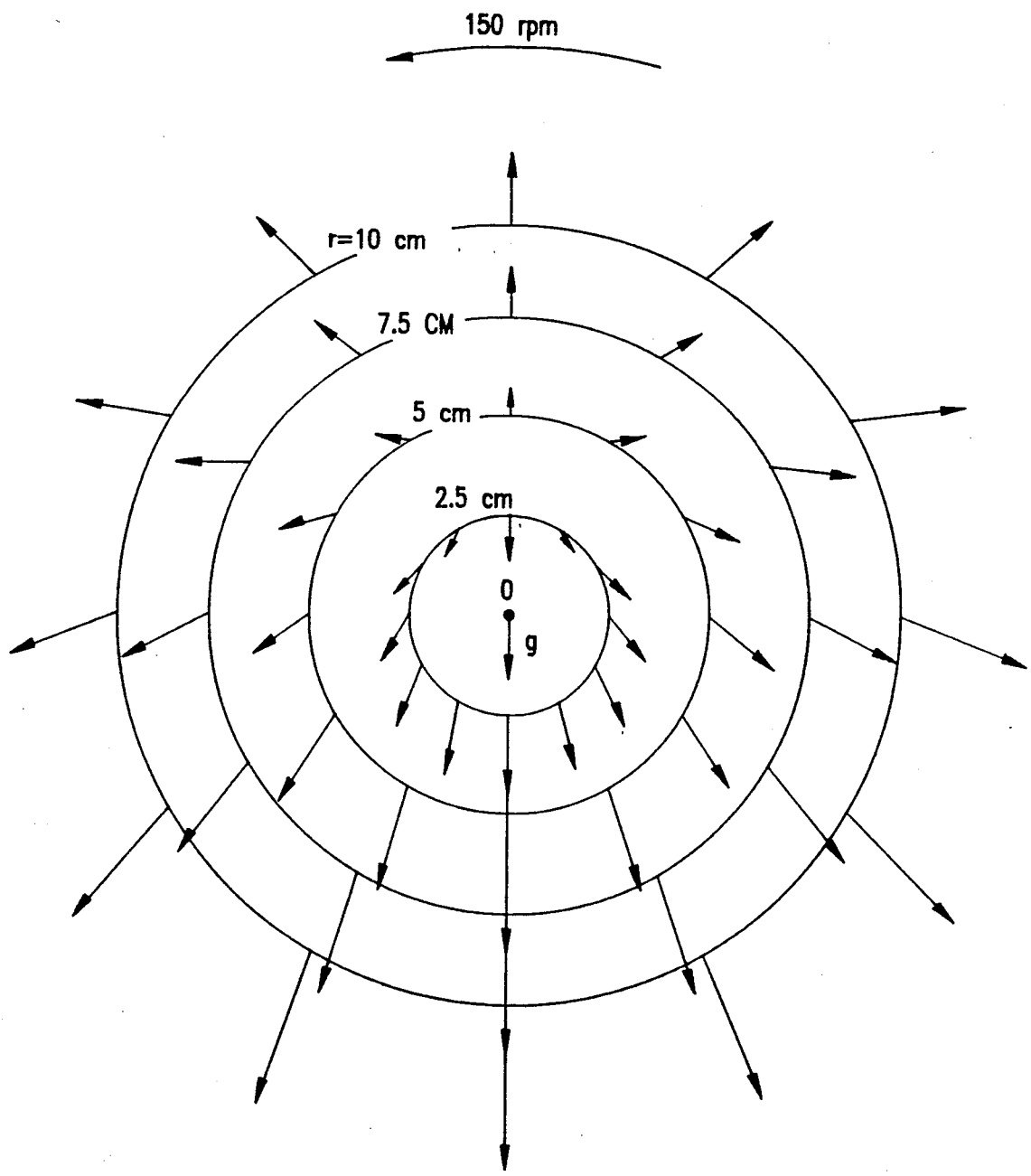
FIG. 17 is a force diagram for simple rotation of a column.

Slow rotation of a coil around the axis positioned horizontally in the gravitational field generates an Archemedian screw force which drives all objects of different density toward one end of the coil, which is known as the "head" end, or the other end of the coil, which is known as the "tail" end. When such a coil contains two mutually immiscible solvent phases, each phase is competitively pushed toward the head of the coil and the result is that the two phases establish a hydrodynamic equilibrium where each phase occupies nearly equal space in each helical turn on the head side. As the rotational speed of the coil is increased, the centrifugal force field produced by the rotation is superimposed on the gravitational field resulting in an asymmetrical distribution of the force field between the upper and the lower halves of the coil (FIG. 17). This in turn alters the hydrodynamic equilibrium state in such a way that one of the phases (head phase) generally the heavier phase in this case, dominates the head of the coil. When the rotational speed reaches the critical range, the two solvent phases are completely separated along the length of the coil the heavier phase entirely occupying the head side and the lighter phase occupying the tail side. This unilateral hydrodynamic distribution of the two solvent phases, when combined with a strong centrifugal force field, provides the basis for the high-speed CCC.

Similar unilateral phase distribution is observed in the coil subjected to various types of planetary motion, such as type J, type X and their hybrids, all of which produce an asymmetrical centrifugal force field between the proximal and distal positions of the rotating coil. However, in these centrifuge systems, the mode of unilateral phase distribution varies according to the physical properties of the solvent system, or in other words, the settling time of the two solvent phases in the gravitational field.

In hydrophobic binary solvent systems with short settling times of 3-10 seconds, the lighter phase is always the head phase, whereas in hydrophillic butanol solvent systems with long settling times of 30-60 seconds, the heavier phase becomes the head phase. In the rest of the solvent systmes with an intermediate range of selltling times of 10-30 seconds, the head phase is determined by the mode of the planetary motion and further modified by the location of the coil on the holder expressed by B.

The effects of a centrifugal force field to the hydrodynamic distribution and motion of two immiscible solvent phases in a coiled column is extremely complex and hardly predictable on a theoretical basis. Nevertheless, it is possible to draw some conclusions about the hydrodynamic effects resulting during type L-X planetary motion in view of the experimental results obtained using the apparatus of the present invention, as well as the results obtained using the various other types of planetary motion producing apparatus.

The above disclosure is provided by way of example only. Obviously, those skilled in the art can construct various devices not specifically described above but incorporating the invention as exemplified herein and by the appended claims.

What I claim is:

1. A synchronous coil planet centrifuge for countercurrent chromatography, comprising:
   rotary frame means rotatable about its central axis;
   column holder means mounted on the rotary frame means at an end of a radius of rotation of the rotary frame means and rotatable therewith about the central axis of the rotary frame means;
   a flow-through coil centrifuge column mounted on the column holder and rotatable therewith about the central axis of the rotary frame means, the central axis of the column being perpendicular to and noncoplanar with the central axis of the rotary frame means, and any radius from the central axis of the rotary frame means to the central axis within the column being non-perpendicular to the central axis within the column; and
   rotation means for rotating the column holder and the column about the central axis of the column, the column holder and the column being rotatable about the central axis of the column and rotatable about the central axis of the rotary frame means at the same speed.

2. A centrifuge as defined by claim 1, wherein the rotation means rotates the column holder and the column in a direction opposite to the direction of rotation of the rotary frame means.

3. A centrifuge as defined by claim 1, wherein the central axis of the column is spaced 5-15 cm from the central axis of the rotary frame means.

4. A centrifuge as defined by claim 3, wherein the central axis of the column is spaced 10 cm from the central axis of the rotary frame means.

5. A centrifuge as defined by claim 1, further comprising a counterbalancing means symmetrically mounted in the rotary frame means opposite the column for counterbalancing the rotation of the column around the central axis of the rotary frame means.

6. A centrifuge as defined by claim 5, wherein the counterbalancing means comprises a second flow-through coil centrifuge column.

* * * * *